(12) United States Patent
Vitzthum et al.

(10) Patent No.: US 6,699,698 B1
(45) Date of Patent: Mar. 2, 2004

(54) METHOD AND SAMPLE MOUNT SYSTEM FOR THE IN SITU SEPARATION AND ENRICHMENT OF SUBSTANCES

(75) Inventors: Frank Vitzthum, Hildrizhausen (DE); Jürgen Bernhagen, Tübingen (DE); Elkin Bentsian, Stuttgart (DE); Herwig Brunner, Stuttgart (DE); Georg Geiger, Pforzheim (DE)

(73) Assignee: Fraunhofer-Gesellschaft Zur Forderung Der Angewandten Forschung E.V. (DE)

( * ) Notice: Subject to any disclaimer, the term of this patent is extended or adjusted under 35 U.S.C. 154(b) by 0 days.

(21) Appl. No.: 09/913,619
(22) PCT Filed: Feb. 14, 2000
(86) PCT No.: PCT/EP00/01201
§ 371 (c)(1), (2), (4) Date: Dec. 22, 2001
(87) PCT Pub. No.: WO00/49173
PCT Pub. Date: Aug. 24, 2000

(30) Foreign Application Priority Data

Feb. 15, 1999 (DE) .......................... 199 06 277

(51) Int. Cl.$^7$ ........................... C12N 13/00; C12M 1/42
(52) U.S. Cl. ................................. 435/173.6; 435/285.2
(58) Field of Search ........................... 435/173.6, 285.2

(56) References Cited

U.S. PATENT DOCUMENTS

| 5,362,895 | A | 11/1994 | Engelhardt Heinz et al. |
| 5,612,207 | A | 3/1997 | Nicolau et al. .......... 435/173.6 |
| 5,676,646 | A | 10/1997 | Hofmann et al. .............. 604/4 |
| 5,695,650 | A | 12/1997 | Held .......................... 210/748 |

FOREIGN PATENT DOCUMENTS

| DE | 3733927 | 4/1988 |
| DE | 3735702 | 3/1989 |
| WO | 9708293 | 3/1997 |
| WO | 9802399 | 1/1998 |
| WO | 9848913 | 11/1998 |
| WO | 9854306 | 12/1998 |
| WO | 9928742 | 6/1999 |

OTHER PUBLICATIONS

Römpps Chemie–Lexikon, Dr. Otto–Albrecht Neumüller, Franckh'sche Verlagshandlung, Stuttgart, 1972, pp. 638–639.

Primary Examiner—Hankyel T. Park
(74) Attorney, Agent, or Firm—Ostrolenk, Faber, Gerb & Soffen, LLP

(57) ABSTRACT

The present invention relates to a method and an apparatus for separating substances from or in biological materials.

45 Claims, 10 Drawing Sheets

Figure 1:
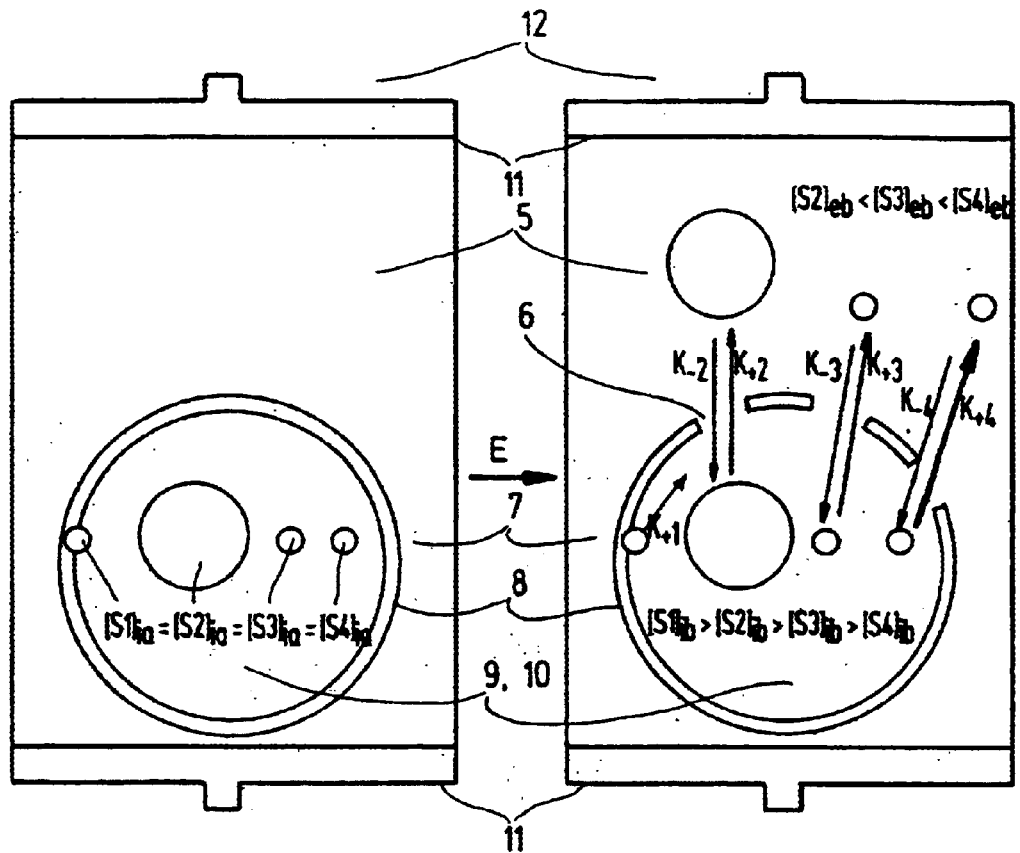

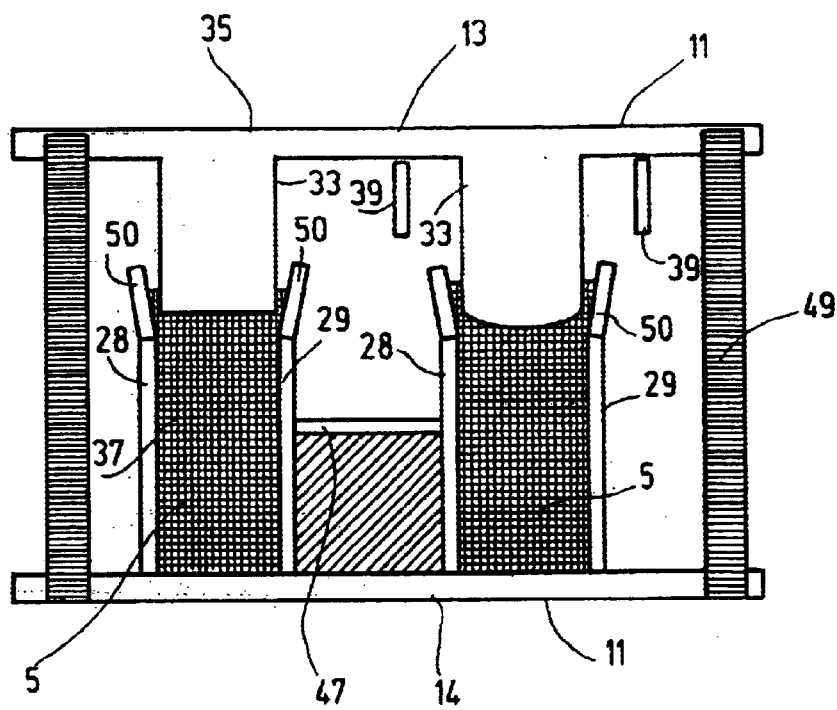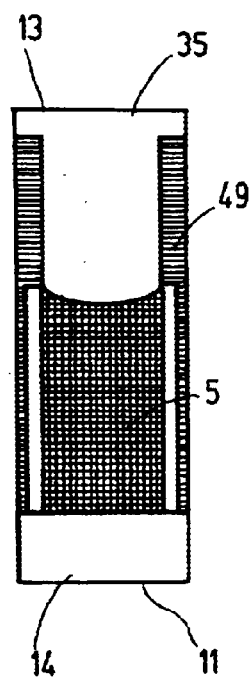
Fig.9a  Fig.9b
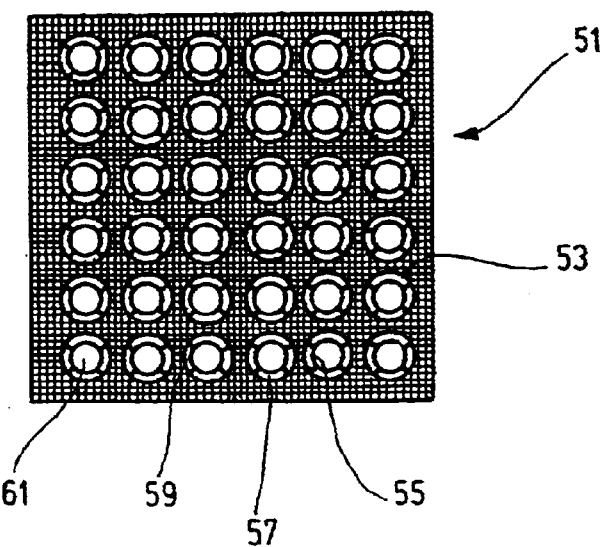
Fig.10

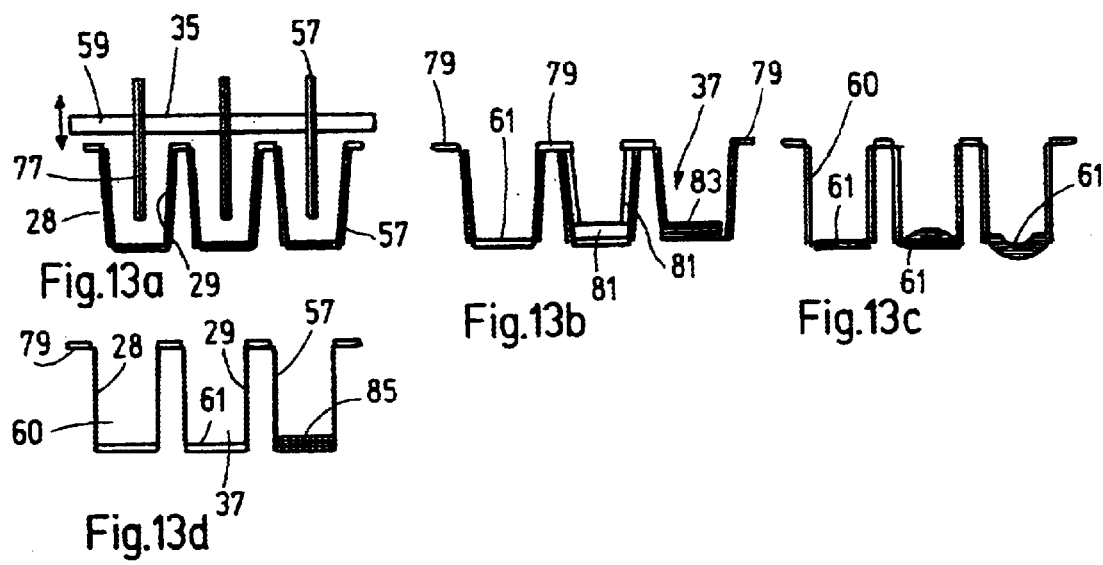

METHOD AND SAMPLE MOUNT SYSTEM FOR THE IN SITU SEPARATION AND ENRICHMENT OF SUBSTANCES

DESCRIPTION

The invention relates to a method and an apparatus for the selective in situ separation and enrichment of substances.

Separation, isolation and disintegration constitute a unit in most separation methods in biology and medicine. Biological material is disintegrated for the purpose of subsequent enrichment, separation or isolation of individual substances or groups of substances or compartments.

The isolation of substances from the most diverse biological materials has been a long-standing practice. Both unambiguous characterization and use in various fields such as pharmacy or medicine, for example, in most cases require the chemically uniform compound, i.e. the pure substance. Within the entire life science sector, therefore, separation methods represent one of the most important foundations for the identification of substances and their use. Said isolation or separation often constitutes a problem, depending on the specific isolation task, for example regarding the purity of the substance to be isolated.

The isolation, separation or disintegration of biological material, for example organisms, tissues, biological cells, organelles, micelles, viruses etc., as a rule constitutes the first step in the analysis or extraction of cell constituents. Such constituents can, for example, be nucleic acids, proteins, metabolites, pigments etc. As the quality of all subsequent steps is determined by the disintegration of the biological material, said disintegration occupies a key position. Novel disintegration methods are therefore of interest for a multiplicity of procedures and have a proportionately large potential for being marketed profitably as a product. Disintegration methods are a prerequisite, in the same way as explained above for the separation methods, for life science fields, for example genomics, proteomics and many others. Methods of disintegrating biological material are not universal, but are geared very specifically to the particular requirements. The known methods—mechanical and non-mechanical disintegration methods—are toxic, expensive, time-consuming and laborious, as well as being limited to specific applications. Moreover, there is a high risk of cross-contamination which has a major impact on the quality of all subsequent process steps, especially in sensitive detection methods such as, for example, the PCR-based nucleic acid detection methods. With the known mechanical methods, moreover, standardization and automation is more difficult, or it is virtually impossible to combine them with separation and isolation methods.

The standard separation and isolation methods include filtration, centrifuging, crystallization, distillation, extraction, electrophoresis, chromatography and magnetism-based methods.

Finally, a distinction is drawn between analytical and preparative methods. Analytical methods are used to detect specific substances in mixtures, while preparative methods are employed for concentrating or extracting larger quantities of as pure a substance as possible.

The use of pulsed electric fields for separation purposes has not been known hitherto.

Instead it is known to use such fields within the context of electroporation (Prausnitz, M. R. et al., in Biophysical Journal 66 (1994), 1522–1530, U.S. Pat. No. 5,019,034, U.S. Pat. No. 5,273,525, U.S. Pat. No. 5,304,120, U.S. Pat. No. 5,389,069, U.S. Pat. No. 5,422,272). With electroporation, from one to at most ten electric pulses (impulse number) are used, as a rule, over the particular treatment time. Depending on the pulse frequency, the treatment duration is at most a matter of seconds, the field strength of the pulses being chosen such that the critical voltage ($V_c$, equal to about 1 volt) across the membrane of the cell to be electroporated is exceeded (with spherical objects, the relationship $v=3/2\ E_0 r$ applies, where r is the cell radius). Electroporation is generally carried out under mild conditions, i.e. for example at room temperature, it being essential not to exceed or drop below the maximum physiologically acceptable temperature of the respective target organism or target cell (U.S. Pat. No. 5,466,587, U.S. Pat. No. 5,545,130, U.S. Pat. No. 5,547,467, U.S. Pat. No. 5,749,847).

Similar conditions are employed with cell fusion, the emphasis here too being on the choice of the mildest conditions possible, to achieve a high success rate in the fusion aimed for ("Electroporation and Electrofusion" in: Cell Biology, Plenum Press, New York and London (1989), editors: Neumann, E., Sowers, A. E. and Jordan, C. A.).

Finally, to achieve complete disruption of biological cells, pulsed electric fields are likewise used in some cases, the cell constituents being released uncontrolledly. In the process, pulse numbers greater than 20,000 are generally used, the field strength as with electroporation generally being above the critical voltage ($V_c$) of 1 volt across the membrane of the cell to be disrupted. The temperatures used for disruption of the biological cells are generally quite high, i.e. they are far above the physiologically suitable temperatures, since the aspect of cell preservation no longer plays a part and, in contrast, the disruption is to be accelerated and completed by employing extreme conditions (U.S. Pat. No. 5,235,905, U.S. Pat. No. 5,447,733, U.S. Pat. No. 5,393,541).

It is hitherto unknown, by means of the conventional methods, for biological material to be sorted, separated and disintegrated and for substances to be released and to be concentrated or isolated directly, or to be purified. Conventional methods, especially separation methods are generally preceded by a time-consuming and expensive sample preparation after cell disruption or work-up, especially sorting and/or disintegration, of the biological material. Thus, the biological material is often first homogenized and lysed, and then is subjected to further processing steps and finally to the separation method. Only in exceptional cases can the homogenate be subjected directly to a separation method. Usually, however, the homogenate is then centrifuged and the supernatant as a crude extract is subjected to a separation method, first requiring adjustment of pH, ionic strength and other parameters.

The object of the invention is therefore to provide a method of separating and disintegrating substances from and/or on biological materials, which renders time-consuming and expensive sample preparation unnecessary and in a single process step leads to the selective in situ release and/or separation of the desired substance(s), a further object of the method being to enable a universal, standardized and consequently automated separation or disintegration of biological material, e.g. organisms, tissues, cells, organelles, micelles, viruses etc., in conjunction with the release of the constituents.

The present invention achieves this object by providing a method for the selective in situ separation of one or more substances from a substance mixture present in a liquid medium by means of a stationary and a mobile phase, wherein the stationary phase is a constituent of a biological material present in the liquid medium and the mobile phase is the liquid medium and wherein the biological material present in the liquid medium is subjected to pulsed electric fields having a field strength of up to 200 V/cm. The substance mixture to be separated can, prior to the separation, disintegration, isolation or enrichment according to the invention, be present in the biological material, or outside it, or both. This means that the substance mixture can be present directly in the liquid medium or enclosed in the biological material in the liquid medium. Preferably, in the process, i.e. during and/or after the treatment with the pulsed, electric fields, one or more desired substances are released from the biological material, are concentrated in the liquid medium and can then be separated from the biological material by means of conventional methods such as e.g. centrifuging or filtration of other, undesirable substances and/or the biological material. In a further preferred, alternative embodiment of the invention, one or more substances are concentrated in the biological material, thus abstracted from the liquid medium outside the biological material, and the liquid medium is then separated from the biological material outside the biological material, for example by centrifuging or filtration.

In a preferred embodiment the invention therefore envisages a purification of one or more substances being carried out directly in situ with the biological material, the substance(s) being released in situ in a single step and being separated from other undesirable substances. The present procedure in a preferred embodiment therefore combines the steps of cell disruption and substance isolation. In so doing, the biological material, especially its solid components such as cell skeleton and membranes, serves as a kind of stationary phase, while the liquid medium, both inside and outside the biological material, can be regarded as the mobile phase. The method is distinguished by extraordinary simplicity and speed, no longer demanding either a time-consuming sample preparation requiring a large amount of material, or cell disruption. Depending on the biological material, various types of interaction can be utilized simultaneously for the separation or the enrichment of substances.

The method is a method for the separation, isolation and/or disintegration of biological material in an electric field having a field strength of up to 200 V/cm. The method can be utilized, in particular, for cell disruption requiring little time and material.

The method is universally applicable and can be used, for example, for the separation of pharmacologically interesting proteins or for determining multiple equilibria between various substances in biological systems.

In connection with the present invention, the term "biological material" relates to spatial units enclosed by lipid or lipoprotein layers having a single- or two-layer structure, i.e. compartments such as cells, especially human, animal, vegetable, yeast or bacterial cells, cell aggregates, remnants or parts thereof, cell compartments such as endoplasmatic reticulum, plastids, mitochondria or cell nuclei, fused cells or cells undergoing division, artificial cell systems, liposomes or other multicomponent systems of natural or synthetic origin. The biological material includes a solid component, for example cell skeleton and membranes, also referred to as the stationary phase, and a liquid component, e.g. cytoplasmatic fluid.

In connection with the present invention, the "separation of one or more substances" refers to the preferably essentially osmosis- or diffusion-driven operation of specifically changing concentrations of one or more substances inside and outside the biological material, especially that of separating one or more substances from other substances, the one or more substances being selected from a selection of substances likewise present in the liquid medium i.e. from a substance mixture. The electric field applied also allows electrophoretic effects to serve or to be utilized as a driving force for increasing or decreasing the concentration of a substance.

In connection with the present invention, the term "substance(s) to be separated" relates to all substances that can be separated by means of the method according to the invention, especially nucleic acids such as DNA and RNA, in cyclic or linear form, proteins or peptides including those in derivatized form such as glycoproteins, or carbohydrates, including those in derivatized form such as proteoglycans. Of course it is also possible to separate other substances, be they of natural or synthetic origin, such as pigments, metabolites, natural substances, synthetic macromolecules and the like. The term "substance" does not, for example, cover the solvent, e.g. water.

In connection with the present invention, the term "enrichment" refers to an increase in the concentration and "depletion" to a decrease in the concentration.

In connection with the present invention, the term "disintegration" refers to a process which modifies the state of order of biological material or which initiates or accompanies the modification. A cell, especially one without defects, has a high state of order which, for example, can be altered by lytic processes at the cell membrane, as a result of compartments of the cell diffusing into the solution surrounding it. For the purpose of the invention, a method of separation, especially of selective separation, and/or enrichment can also be a disintegrating method.

In connection with the present invention, the term "liquid medium" refers to a preferably aqueous solution, suspension or emulsion. The liquid medium within the biological material can differ, in terms of its composition, from the composition outside the biological material, for example be in the form of plasma within a cell and in the form of saline outside the cell.

The present invention is based, inter alia, on the use of pulsed electric fields to treat biological material, the generated potential difference across the membrane of the biological material preferably, depending on the biological material itself, on pulse number, pulse shape, treatment duration and temperature, being below the critical voltage. $V_c$, resulting in the formation of permanent or transient pores of different diameters in the membrane. According to the invention it is of course also possible to provide potential differences across the membrane of the biological material which are above the critical voltage $V_c$. Through the pores formed, extracellular substances can pass into the biological material, especially the cell, intracellular substances conversely being released. The release or uptake of the substances depends on the strength and type of the interactions between these substances and between the substances and the biological material, on the lifetime and on the diameter of the pores. The biological material, including any intracellular matrix present of the membranes and cell walls present, e.g. tubulines etc., as the "cell skeleton", takes part in the separation.

In a preferred embodiment, the invention provides a method for a chromatography-like, selective separation of substances in situ by means of a stationary and a mobile phase, wherein the stationary phase is a constituent of the biological material and the mobile phase is a liquid medium and wherein the biological material present in the liquid medium is subjected to pulsed electric fields having field strengths of up to 200 V/cm and the substance(s) of interest are released from the biological material, are concentrated in the liquid medium outside the biological material and are separated from the biological material. The invention therefore advantageously provides for the enrichment or separation to take place in situ, i.e. in and on the biological material containing the substances of interest, without the biological material having to be disrupted prior to the separation or enrichment. For separation purposes, centrifuging methods can be used according to the invention which are able to separate the substance(s) from the biological material. Alternatively, according to the invention, provision can be made for the separation of the biological material from the liquid medium present outside the biological material to be performed by filtration, crystallization, extraction, electrophoresis, chromatography or by means of similar methods.

A prerequisite for implementing the in situ separation method according to the invention is that the various parameters which affect the separation efficiency, such as field strength, pulse number, pulse shape, treatment duration, temperature, solution, type of biological material etc., be optimized for each isolation task to be carried out.

In a preferred embodiment, the invention makes provision for biological material to be disintegrated in a sample mount system, the sample mount system comprising at least one nonconductive element and two conductive elements, wherein a voltage is applied to the conductive elements and the biological material is exposed in an electric field having a field strength of up to 200 V/cm, particularly in a range of from 5 to 50 V/cm.

In a further preferred embodiment of the invention, the electric field acting on the biological material is homogeneous or inhomogeneous. Preferably, the disintegration or separation of the organisms, cells or compartments takes place in an inhomogeneous electric field.

In a preferred embodiment of the invention, the electric field line density is increased locally. The disintegration or separation, especially selective separation from biological material advantageously takes place in an inhomogeneous electric field in which, for example, the electric field line density can be locally increased.

In a further preferred embodiment it is advantageous for the number of the electric pulses to be above 10. The pulse number can be determined from the product of treatment duration and frequency. Depending on the sample to be treated, the treatment duration can be between a few seconds and a number of hours. The frequencies used in this context should be between a few mHz and more than 1 GHz. Via the selected frequency, it is possible to suitably limit the maximum pulse duration. The pulse duration can be a few nanoseconds but advantageously equally be in the range of a few minutes.

In a further preferred embodiment of the invention, the pulsed electric fields used can have various pulse shapes. For example, exponential or sinusoidal pulse shapes, or alternatively rectangular pulses and/or triangular pulses can be used. Furthermore it is advantageous for the voltage of the individual pulse to fluctuate within itself, for example sinusoidally. If DC voltage pulses are used, the polarity of the pulses can be reversed continuously or at intervals, thus allowing AC voltage pulses to be applied. Advantageously, a superposition of DC and AC voltages is also possible, to achieve optimal enrichment, separation and/or disintegration. It is equally possible, for example, to combine various pulse shapes and/or pulse intensities, i.e. voltage levels and pulse duration, in a variable manner; in the case of exponential pulse shapes the pulse duration is expressed by the time constant $(\tau)$: $\tau=CR$ (C: capacitance, R: resistance).

In a further advantageous embodiment of the invention it is also possible, for example, using suitable apparatus, to employ polyphase current, i.e. three-phase current. This allows the generation of, for example, sinusoidal AC voltages with a phase difference of 120° or 240°.

In this context, the invention, in a preferred embodiment, provides for the use of pulse numbers, i.e. pulses per treatment duration, of at least 15, preferably from 15 to 19,000, especially from 5000 to 12,000. In a further preferred embodiment, the field strength of the pulses is far below the critical voltage $V_c$ applied across the membrane or cell wall of the biological material, for example the cell or the liposome. Alternatively, however, according to the invention, a field strength of the pulses can be provided which is above the critical voltage $V_c$ applied across the membrane or cell wall of the biological material. Preferably, the field strength of the pulses is from 0 to 200 V/cm, from 0.001 to 200 V/cm, from 0.01 to 200 V/cm, from 20 to 60 V/cm and particularly from 30 to 50 V/cm.

According to the invention it is possible, in a preferred embodiment, to let a pulse of high electric field strength be followed by a second pulse of lower field strength, in order thus to assist electrophoretic effects. Advantageously, the pulses can be superposed by means of DC voltage.

In a further preferred embodiment, the invention makes provision for carrying out the chromatographic separation and temperatures of between −30 and +90° C., particularly from 50 to 55° C. Particularly preferred are temperatures which, under the given constraints, are below the temperatures resulting in cell disruption and above or below the physiological, i.e. naturally obtaining temperatures of the biological material.

Advantageously, the invention, in a further preferred embodiment, makes provision for the disintegration to be carried out at temperatures of between 0 and 100° C., particularly between 20 to 80° C.

In a further preferred embodiment, the invention makes provision for the treatment duration, within which the separation is carried out via the use of pulsed, electric fields, to be from a few seconds, e.g. from 2 to 6 seconds, up to hours, e.g. from 3 to 5 hours.

In a further preferred embodiment, the invention makes provision for the frequency of the pulses to be from 0.1 Hz to 40 GHz.

Finally, the invention makes provision, in a further preferred embodiment, for the pulse duration to be from 25 ps to 50 min., particularly 15 μs.

Electroporation and electrofusion, optionally in combination with dielectrophoresis, customarily involve the use of hypoosmolar media whose conductivity is as low as possible. Electrolytic effects, change in pH and release of cytotoxic ions from the electrodes are thus minimized. Since a main objective of these methods is to maintain the vitality of the cells, the composition of the medium is critical. A further reason for using such media in the methods listed is the shape of the cells in hypoosmolar solutions; they become rounder. This facilitates the calculation of the field strength to be used to achieve the critical voltage $V_c$, said field strength as a rule being lower for spherical objects.

Moreover, the methods predominantly employ media having optimal potassium concentrations, to ensure the vitality of the treated cells. Apart from the osmolarity of the media and the presence of specific ions, conductivity is decisive. In the case of electroporation, electrofusion and dielectrophoresis, conductivity is low, as a rule. In general this is the only way to obtain the field strengths necessary to achieve the critical voltage $V_c$ required for these methods.

Since the vitality of the cells in the case of the in situ separation methods according to the invention is not a major factor, these methods preferably employ isoosmolar media whose conductivities are high, compared with the conductivities customarily used with electroporation, electrofusion and dielectrophoresis. Even so, it is of course possible to employ hypo- or hyperosmolar media having comparatively low or high conductivities. Thus the in situ separation method can dispense with laborious "rebuffering" of the samples. The biological material can be used directly as the "raw material". The conductivity of the medium in the procedure according to the invention, i.e. the in situ separation method, can preferably be from 1 $\mu$S/cm to 2 $\mu$S/cm, particularly from 5 to 20 $\mu$S/cm.

Pharmacologically relevant, low molecular weight proteins such as the human Macrophage Migration Inhibitory Factor (huMIF) cloned and expressed in *E.coli*, with a relative molecular mass of about 12.3 kDa can be purified from the respective cell suspensions via the in situ separation method according to the invention. The in situ separation method according to the invention can also be used in the field of bioreactors.

The method according to the invention can also be used for determining binding equilibria. The method according to the invention makes it possible for pores having a lifetime and size optimally tailored to the equilibrium in question to be induced in liposomes or other biological material. This offers the possibility of utilizing the principles of various methods of determining binding equilibria by means of a single method, i.e. the present method according to the invention. According to the invention it is also possible to employ liposomes filled with ligands, the ligands, after said liposomes have been permeabilized, being able to diffuse freely from the intracellular medium into the extracellular medium until an equilibrium has been established. According to the invention, provision can be made for macromolecules to which the ligands can bind to be present in the extracellular medium, so that the fraction of the bound ligands is removed from the equilibrium and ligands from the intracellular medium continue to flow in until the free fractions of the ligands in both chambers have equalized. After the equilibrium has been established, the concentration of the ligands in the extracellular medium then corresponds to the concentration of the free ligand in the association equilibrium of the intracellular medium. It is therefore possible, once the ligand concentration in the intracellular and extracellular medium has been determined, to determine the concentrations of the free and the bound ligand. Keeping the macromolecular concentration at various ligand concentration constant, it is then possible to determine binding constants.

According to the invention it is also possible for the macromolecule to be provided in the intracellular medium and for the ligand to be provided in the extracellular medium. As an alternative to liposomes, biological cells can of course be used.

According to the invention it is therefore possible for the binding characteristics of macromolecules intrinsic to cells or of expressed macromolecules extrinsic to cells in terms of a specific ligand to be studied in situ.

The invention also relates to the use of pulsed electric fields for the selective in situ separation of substances, the substances being concentrated either in a liquid medium which surrounds biological material or within the biological material, pulse numbers of at least 15, preferably from 15 to 19000, particularly from 5000 to 12000, being used in generating the pulsed electric fields.

In a preferred embodiment, provision is made for the samples to be treated to be applied to matrices, for example membranes or bonded fiber webs. The matrices can either be in direct contact with the conductive elements or, for example, be separated from the conductive elements by liquid zones.

In a further preferred embodiment of the invention, provision is made for the samples to be treated, especially doped matrices or liquids which comprise the biological material, not to be in direct contact with the conductive elements, for example the sample mount system. The contact can advantageously be broken by air, for example by conductive elements not being immersed in the liquid and/or by conductive elements being encased by nonconductive elements. In order to achieve, in particular, field strengths of up to 200 V/cm in the samples thus prepared it is advantageous for higher voltages if required, possibly as a function of the spacing of the conductive elements, to be used on the conductive elements. As the electrical separation, disintegration or enrichment methods permit the preferable use of pulsed electric fields having very low field strengths or advantageously do not require any direct contact of the conductive elements with the sample, the choice of solvent is not restricted. It is possible, for. example, for biological material to be disrupted or enriched or separated even in solutions having high specific conductivities, without incurring the risk of spark discharges. In particular, this provides the option of combining the electrical separation, enrichment and/or disintegration with chemical methods.

In an advantageous refinement of the invention provision is made for the optional use of certain salts, for example chaotropic salts, and detergents, enzymes and others before or during the electrical separation and/or disintegration of course it is also possible to carry out a chemical aftertreatment of the separated or disintegrated samples or suspensions obtained. Advantageously, the combination of a chemical separation, enrichment and/or disintegration with the enrichment, separation and/or disintegration induced or accompanied by electric fields can lead not only to a simple addition of the effects, but also to unexpected and novel synergetic effects.

Chemicals which change and/or stabilize the specific conductivity of the extracellular phase of the cell membrane and possibly the cell interior, can be used to advantage. This has an advantageous effect on the differential potential across the cell membrane, resulting in a change, for example, in the critical voltage across the cell membrane, which is necessary to generate pores, discrete lesions and/or ruptures in the cell membrane. Also possible is the use of suitable chemicals which affect and/or modify the fluidity of the cell membranes. Similarly to the way in which an increase in temperature affects the fluidity of the cell membrane, with an effect on the value of the critical cell membrane voltage, chemicals can advantageously likewise affect the fluidity of the cell membrane, particularly the critical cell membrane voltage. Chemicals and changes in temperature can therefore affect the fluidity of the cell membrane, resulting in an effect on the value of the critical cell voltage. The chemicals may optionally also have additive, lytic properties. Furthermore, the addition of chemicals can advantageously lead to reduced breakdown of cell constituents. For example, the chemical inhibition of nucleases and/or proteases in the extraction of nucleic acids and/or proteins via electrical cell disruption can be of advantage. But other cell constituents, for example metabolites, can likewise be stabilized in this way while being released and after they have been released by electrical cell disruption, particularly during the separation and/or disintegration.

The invention also relates to an apparatus which comprises an nonconductive element and at least two conductive elements, particularly electrodes. In a preferred embodiment, provision is made for the nonconductive element to be designed as a holding means and for conductive elements to be capable of being connected, for example via a cover, to the holding means in such a way that the sample can be disintegrated in the holding means. Alternatively, however, provision can advantageously be made for the holding means to comprise a conductive element. The conductive elements, can include a nonconductive element to allow a voltage to be built up, but it is also possible for the holding means to comprise just a first conductive element and for the second conductive element to be disposed in such a way in a cover for the holding means that it can be positioned so as to be capable of effective connection to the first conductive element designed as a holding means.

The invention also relates to an apparatus for implementing the method according to the invention, particularly a sample mount system or an in situ separation apparatus, the latter being designed as a preferably essentially box-shaped, particularly cuboid housing comprising a baseplate, a cover plate, two side walls and two electrodes designed as side walls. The cover plate has at least one port, with the option of further ports being provided in the cover plate and possibly in the baseplate. These ports can in each case be sealed by a filter which is used to separate off the separated substance or substance mixture. The electrodes can be made of aluminum, alloy steel, carbon, platinum, gold or silver or comprise these on their own or in combination. Preferably, the sample mount system according to the invention also comprises a voltage generator, particularly an HVA apparatus (high voltage apparatus), a frequency generator and a pulse generator.

To enable a high sample throughput in the electrical selective separation, sorting and/or disintegration, it is advantageous to provide separation apparatuses which allow a plurality of samples to be treated in one go. This can be advantageously implemented, for example, by various formats, such as those used in known microtiter plate systems. One example of an advantageous way of generating electric fields involves novel array systems which, for example, consist of a sample mount and a cover. In this way, conductive and nonconductive elements can be advantageously tailored to one another by different arrangements of conductive and nonconductive elements of the sample mounts and the covers, relative to one another. Regarding the covers, for example, cylindrical metal rods, with an additional conductive plate in the cover of the sample mount or at the end of the metal rod can be used. That end of the metal rods which projects into the sample can advantageously be in the form of a sphere. Partial or complete insulation of the metal rods or conductive elements of the cover plate of the separation apparatus and/or of the entire separation apparatus and/or of the sample mount can be of advantage and advisable. Separation apparatuses for the selective separation, and sample mounts for the disintegration, can advantageously be used for the processes of disintegration, separation and/or isolation. To design electrical disintegration arrays so as to be compatible with other methods, there is an advantage in using standardized dimensions. For example, it is advantageous to tailor such an electrical disintegration array or, for example, an individual sample mount to the dimensions of sample mount-containing known PCR instruments, fluorimeters, spectrophotometers and the like. In this context it is particularly advantageous to provide transparent regions, for example in the nonconductive elements, especially the baseplates.

Further advantageous embodiments of the invention can be gathered from the dependent claims.

The invention is explained in more detail with reference to the following examples and the accompanying figures.

Figure 2:
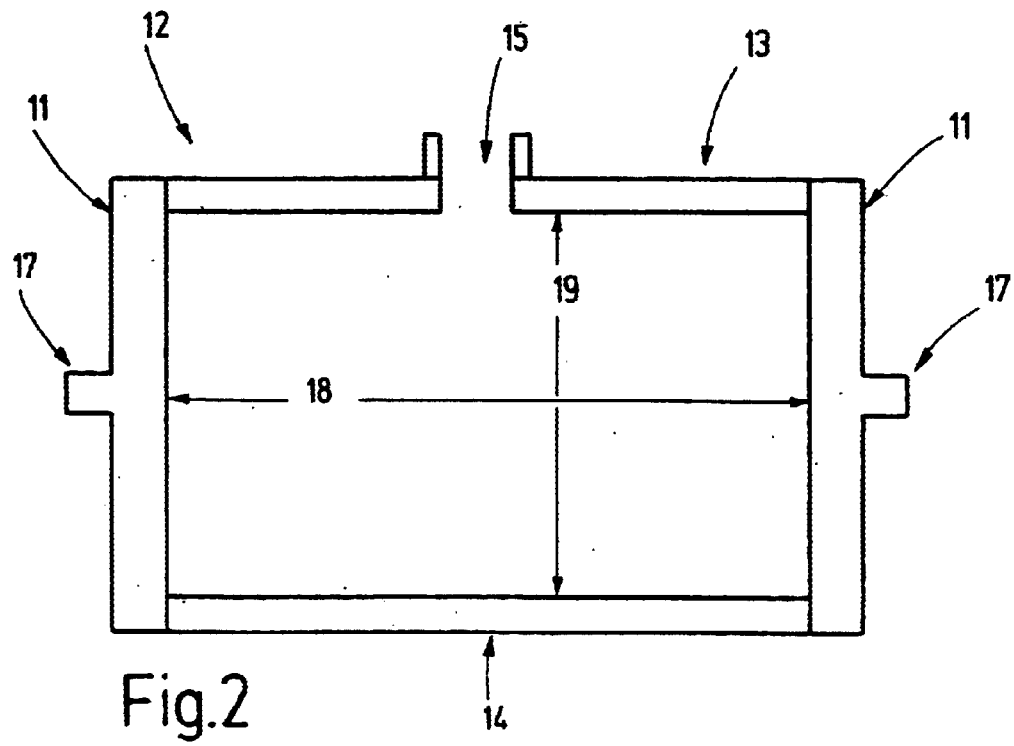
Figure 3:
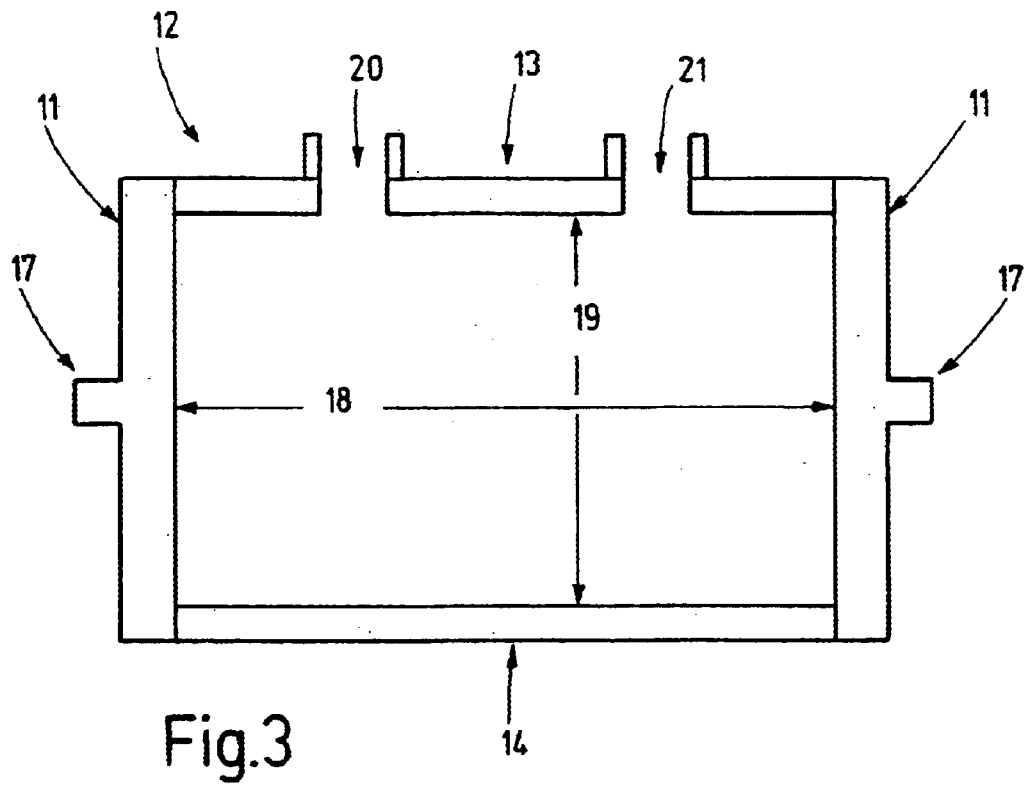
Figure 4:
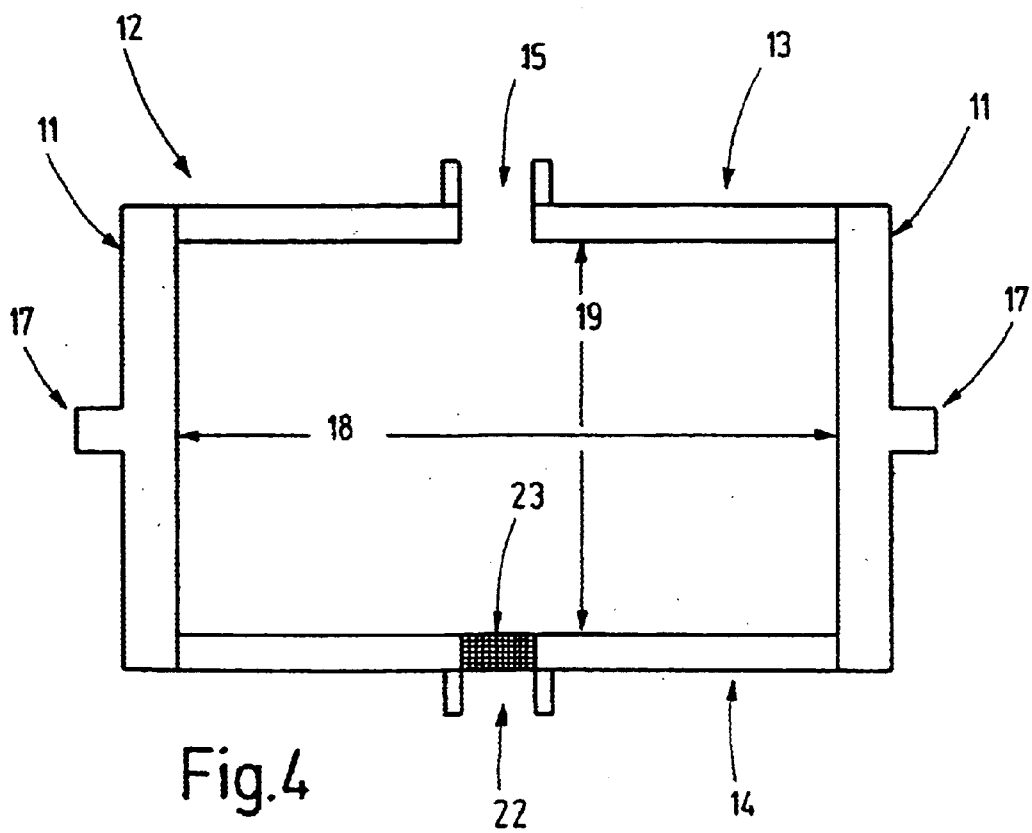
Figure 5:
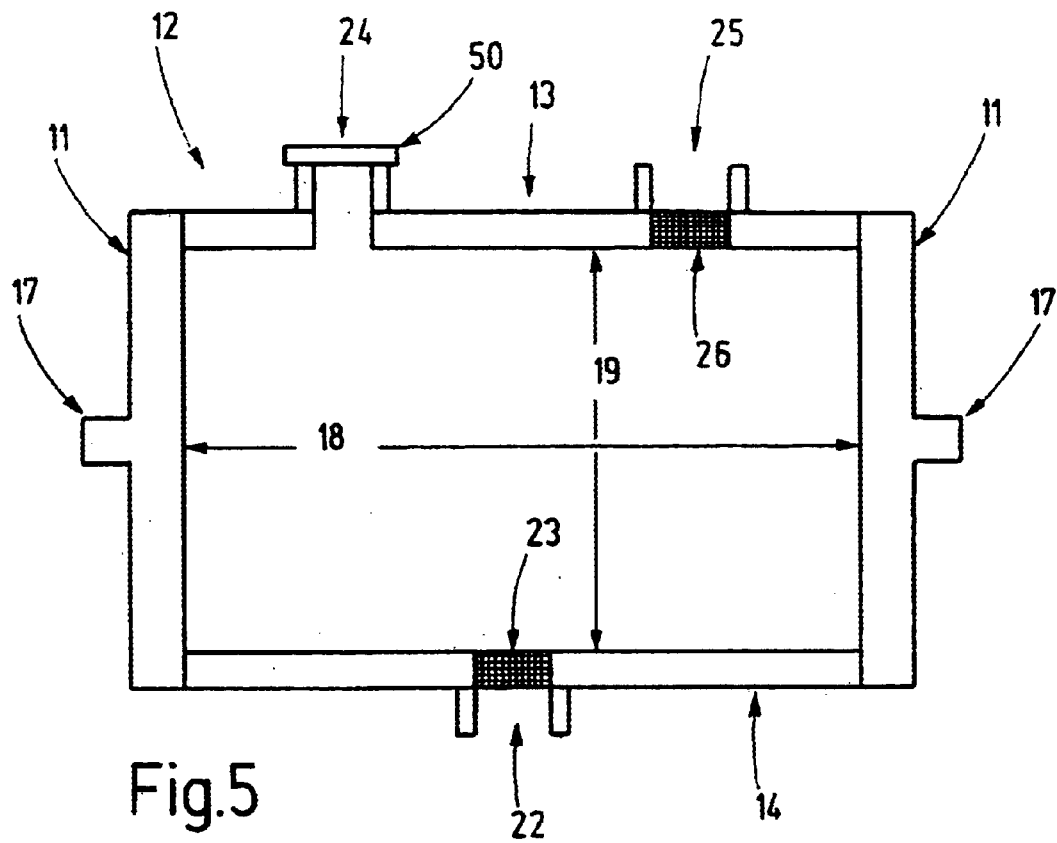
Figure 6:
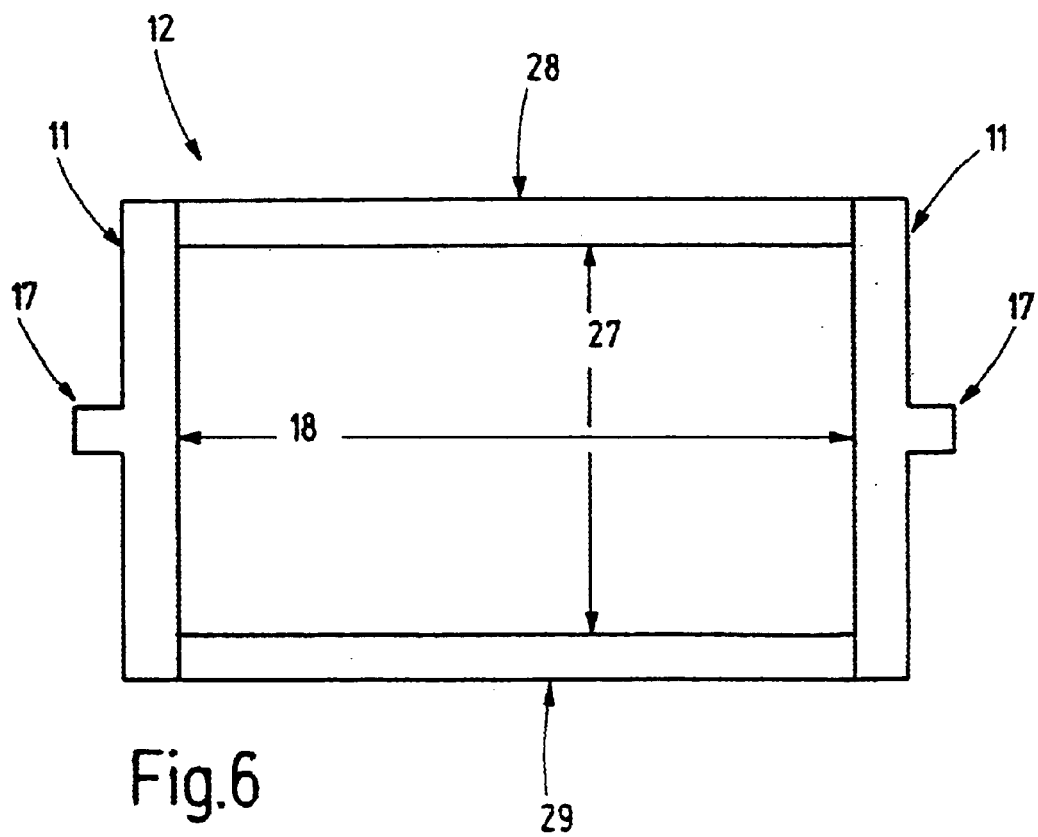
Figure 7:
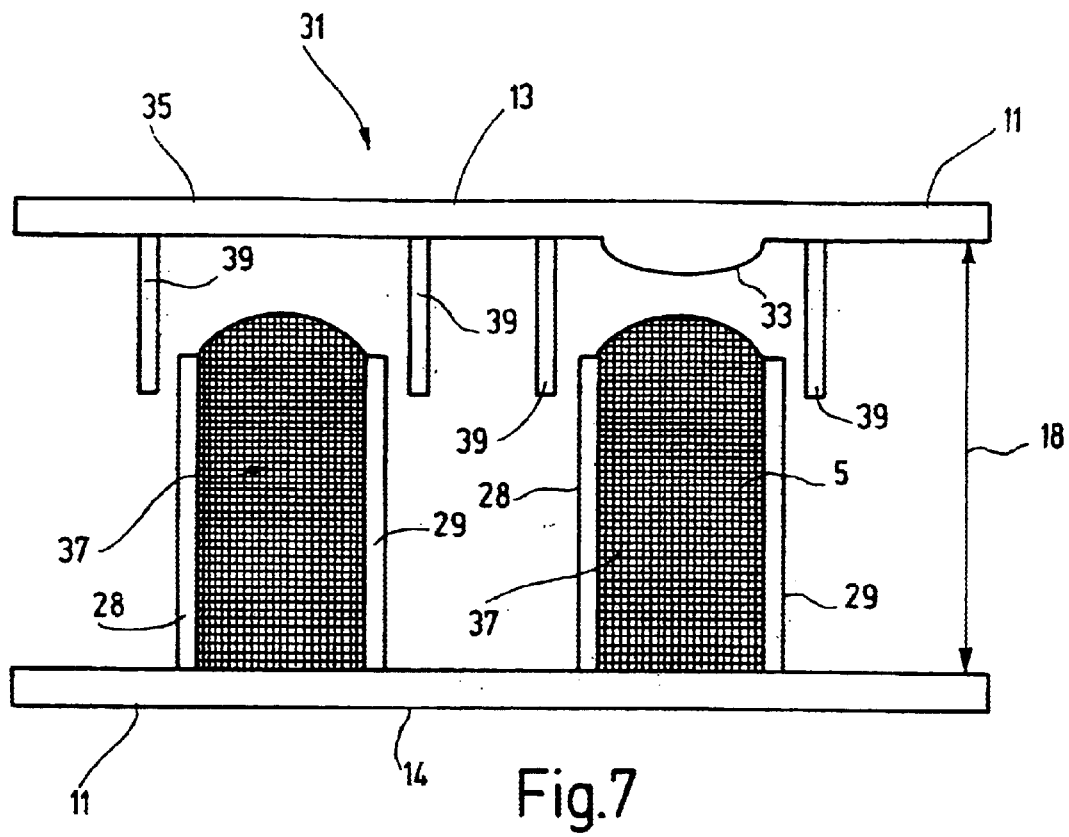
Figure 8:
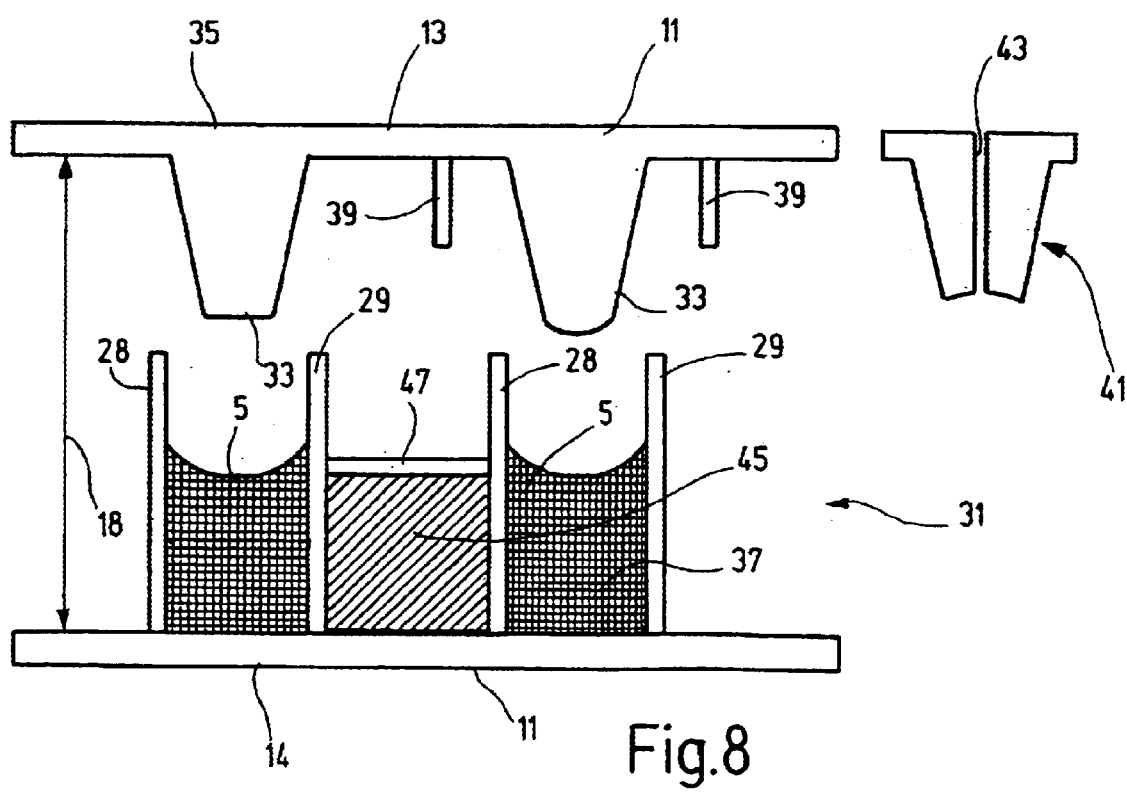
Figure 15:
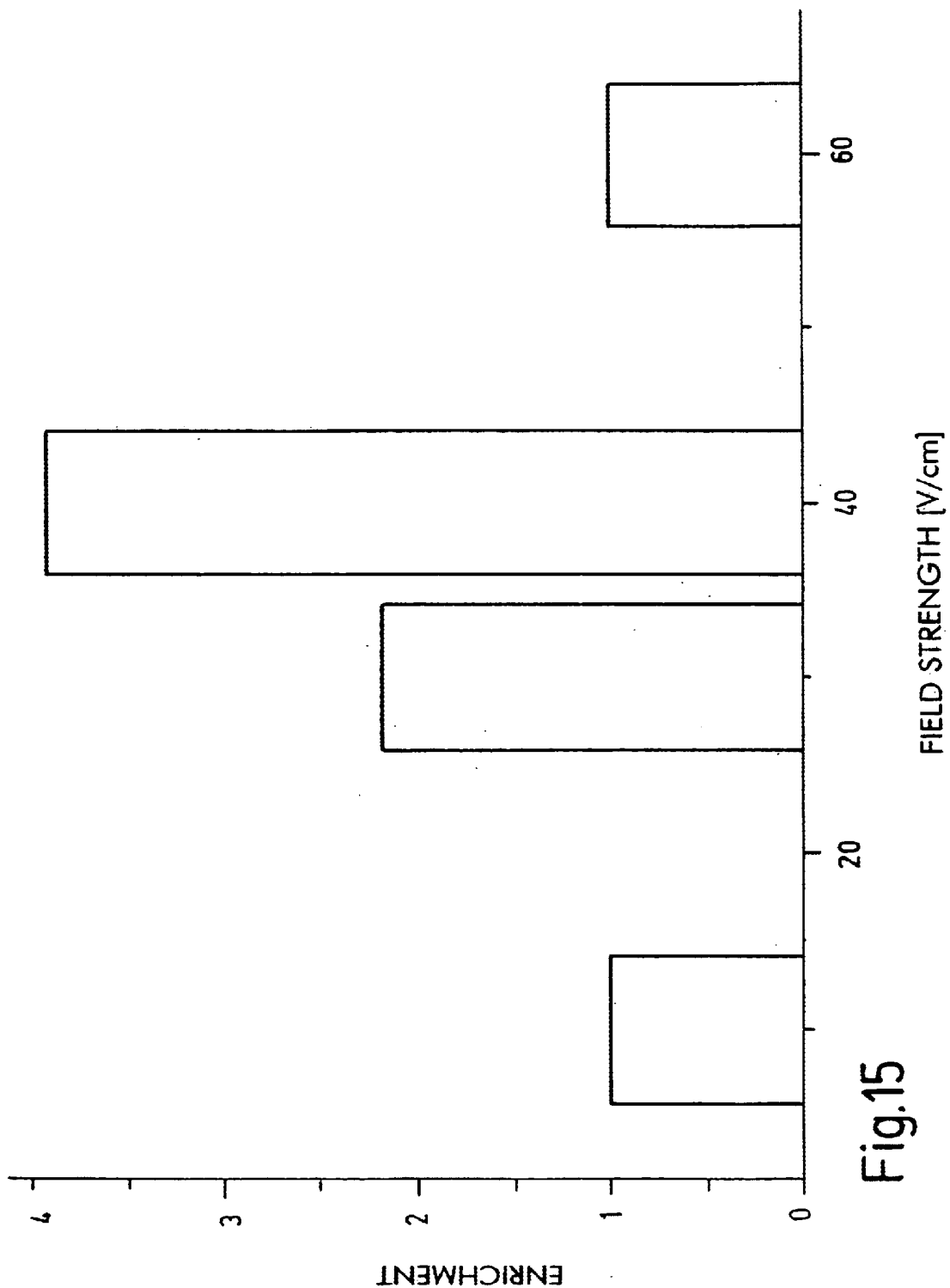
Figure 16:
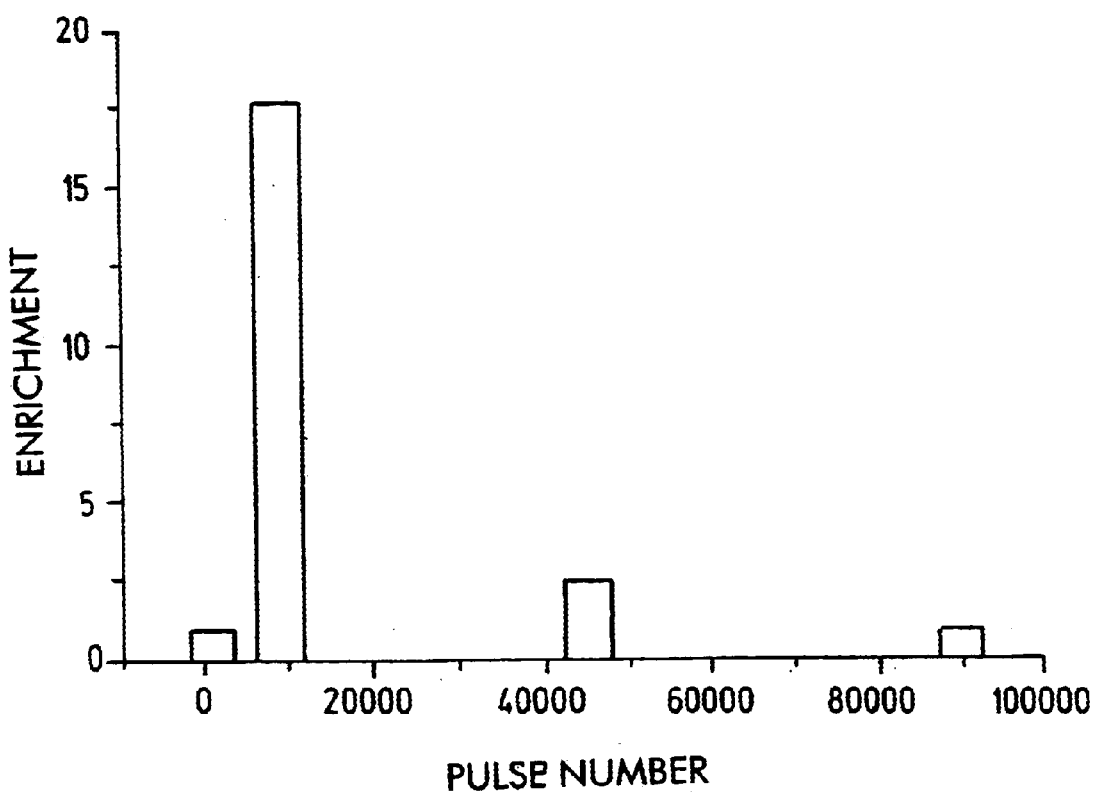
Figure 17:
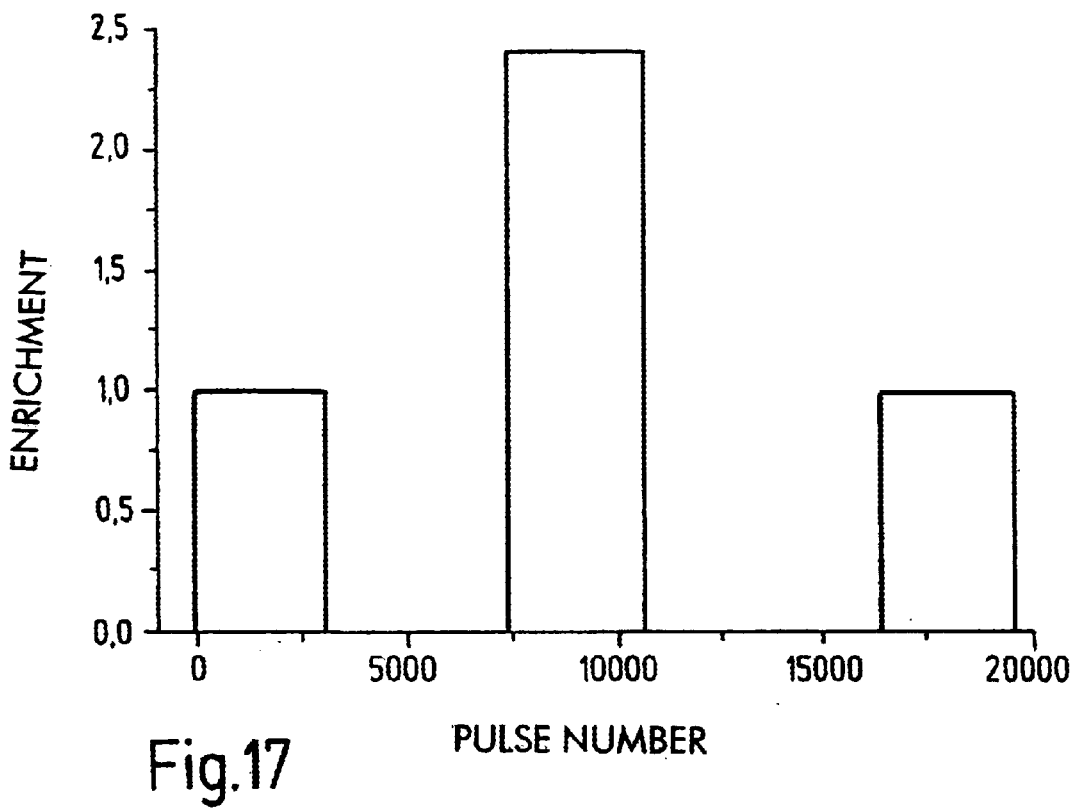
Figure 18:
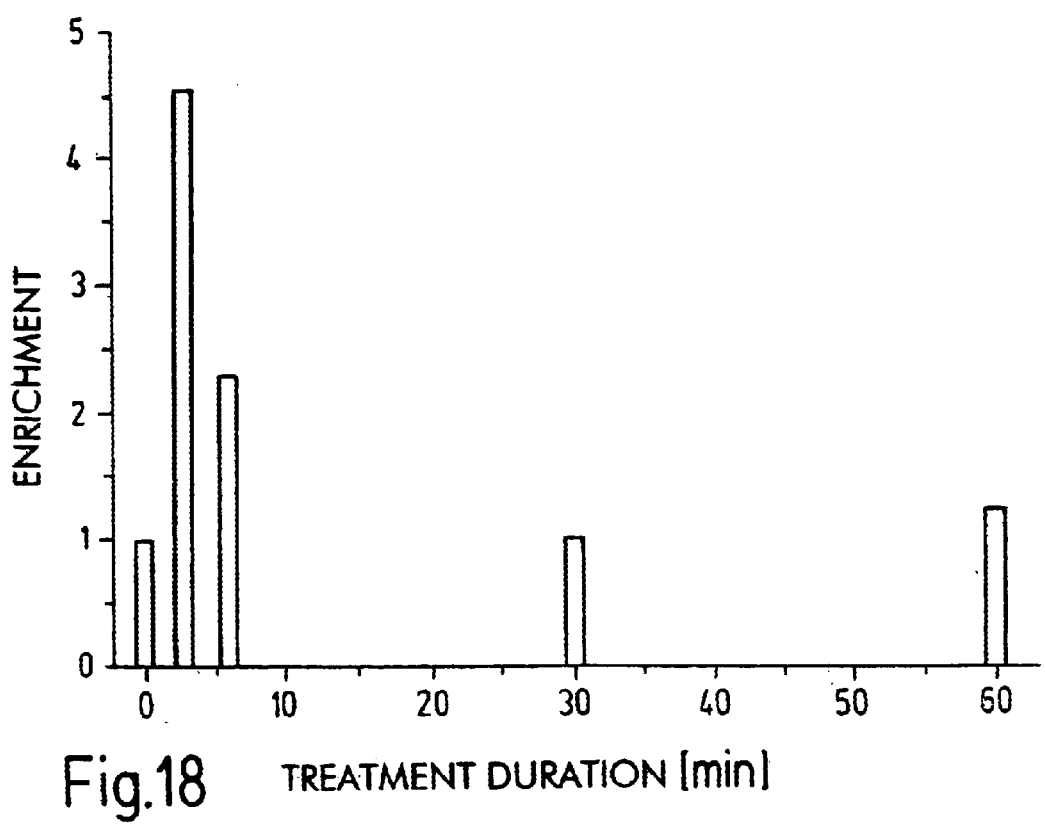
Figure 19:
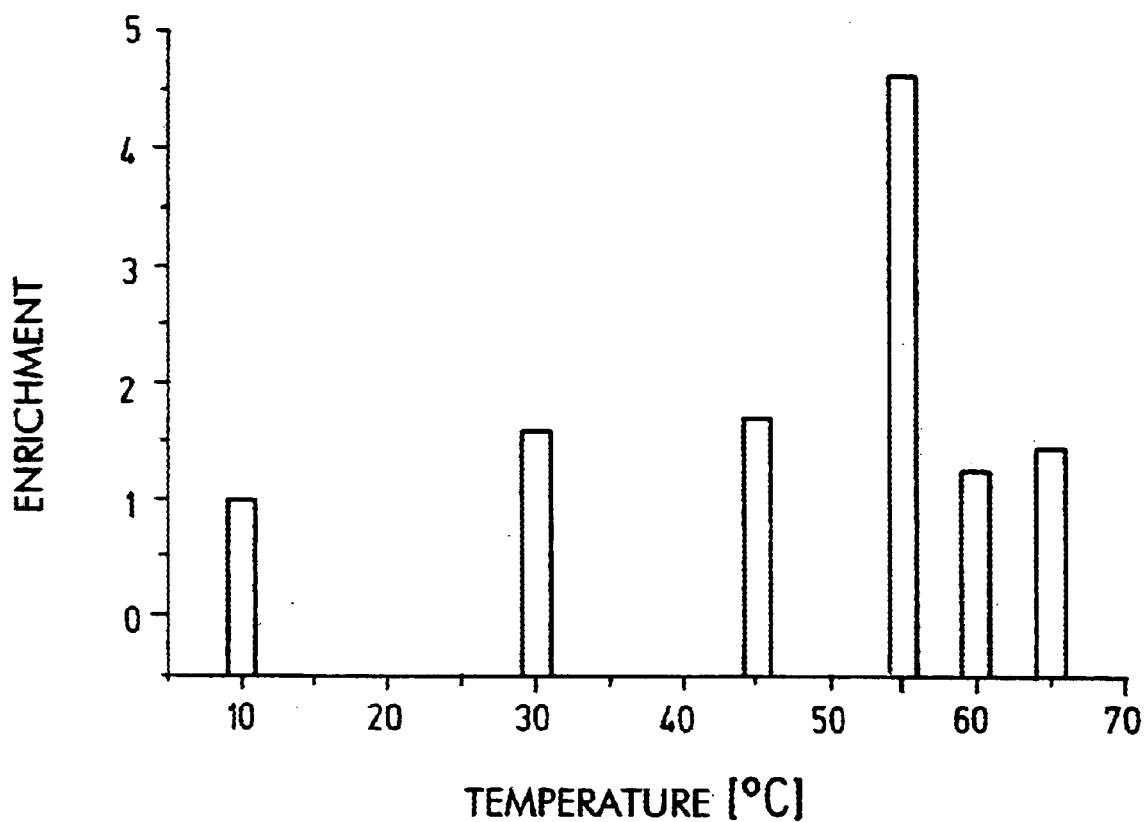

In the figures:

FIG. 1 schematically shows the principle underlying the invention,

FIG. 2 shows an in situ separation apparatus with a port in the cover plate in longitudinal section, FIG. 3 shows an in situ separation apparatus with two separate ports in the cover plate in longitudinal section, FIG. 4 shows an in situ separation apparatus with a port in the cover plate and a port in the baseplate, into which a filter is inserted, in longitudinal section, FIG. 5 shows an in situ separation apparatus with two ports in the cover plate and a port in the baseplate, in longitudinal section, one port in the cover plate and the port in the baseplate being provided with a filter, FIG. 6 shows a cross section through the in situ separation apparatus of FIGS. 2 to 5, FIG. 7 shows a cross section through a sample mount system, FIG. 8 shows a cross section through the sample mount system, with a cover, FIG. 9 shows a cross section through the sample mount system, with a hydraulic seal, FIG. 10 shows a plan view from above of a chip for the separation and/or disintegration, FIG. 11 shows a longitudinal section through sample mount systems, FIG. 12 shows a cross section through individual sample mount system, FIG. 13 shows a longitudinal section through sample mount systems, wherein a holding means comprises conductive elements, FIG. 14 shows a longitudinal section through covers for holding means, wherein these comprise conductive elements, FIG. 15 shows how the enrichment in a substance depends on the field strength, FIGS. 16 and 17 shows how the enrichment in a substance depends on the pulse number, FIG. 18 shows how the enrichment in a substance depends on the treatment duration, and FIG. 19 shows how the enrichment in a substance depends on the separation temperature.

FIG. 1, in a schematic sketch, shows the scenario for the method according to the invention. It shows an in situ separation apparatus 12 in two states, the chamber 12, which in FIG. 1 is on the left, being in the rest state, while the separation apparatus 12 which in FIG. 1 is on the right, is subjected to pulsed electric fields E. The in situ separation apparatus 12 contains a cell 7 in a liquid medium 5 located outside the cell 7. The cell 7 is composed of the intracellular matrix 9, the liquid medium 10 located inside the biological material 7, and the cell wall or cell membrane 8. The stationary phase of the chromatographic system according to the invention is therefore formed by the cell membrane 8 and the intracellular matrix 9, while the mobile phase is formed by the liquid medium present inside and outside the biological materials 7, it being quite possible for the composition of the medium present inside the biological material to differ from that of the medium present outside. Present inside the biological material in the rest state are four different substances S1 S2, S3 and S4, of which S1 is firmly bound to the cell wall 8, while S2, S3 and S4 are present in free form inside the biological material 7. The size shown of the substances S to be separated corresponds to the molecular size of the substances to be separated. Also shown are the two electrodes 11 of the in situ separation apparatus 12.

After the cells 7 in a suitable liquid medium 5 have been transferred into the in situ separation apparatus 12, pulsed electric fields E cause pores 6 to be generated in the cell membrane or cell wall 8 of the cells 7 (right-hand chamber), the field strength E being determined from the quotient of the voltage applied and the spacing of the electrodes 11 in the in situ separation apparatus 12. The lifetime, number and size of the pores 6 depend, inter alia, on the properties of the biological cell 7, its size, shape, structure, the orientation of the cell 7 in the electric field, the pulsed electric fields themselves, i.e. the field strength, the pulse number, the treatment duration of the pulse frequency, the time constant, the pulse duration, the pulse shape, the treatment temperature, the composition of the liquid medium 5, particularly the pH, the ionic strength, the conductivity, the type of ions, the osmolarity, the concentration of the biological material and optionally admixed additive detergents, chaotropics, complexing agents or organic solvents. The chromatographic separation efficiency of the method according to the invention itself depends on the characteristics and the resulting interactions of the substances S1, S2, S3, S4 to be separated and of the stationary and the mobile phase. Also responsible for the separation efficiency of the method according to the invention is the relative movement of stationary and mobile phase with respect to one another.

The properties of the substances S1, S2, S3, S4 to be separated and of the stationary and mobile phase in terms of their ability to enter into electrostatic, hydrophobic, aromatic interactions and hydrogen bonds depends on the composition of the liquid medium 5. The treatment temperature and the properties of the electric field E used also matter. The size of the substances S1 to S4 to be separated is independent, as a rule, of these factors. The method according to the invention therefore utilizes all the interactions of the customary chromatographic methods such as gel permeation chromatography, ion exchange chromatography, affinity chromatography and hydrophobic interaction chromatography for the separation.

Significant for the relative motion of stationary phase against mobile phase is the composition of the liquid medium present inside the biological material 7 and that present outside the biological material 7 with respect to osmotic and diffusion-controlled processes. The invention additionally utilizes electrophoretic effects which arise as a result of the electric field being applied.

The above-described parameters affect the rate constant $k_+$ of the transfer of the substances S1 to S4 from the biological material 7 into that region of the liquid medium 5 which is located outside the biological material 7. The same applies to the rate constant $k_-$ of the transfer of the substances S1 to S4 from the liquid medium 5 located outside the biological material 7 into the region inside the biological material 7. If the lifetime of the pores 6 is sufficient to permit an equilibrium state to be established, the quotient of $k_+$ and $k_-$ defines an equilibrium distribution K. If the lifetime of the pores 6 is less than the time it takes to establish the equilibrium state, an apparent equilibrium constant $K_{app}$ obtains. The procedure according to the invention applies to both cases. The different properties of the substances S1 to S4 result in different partition constants, so that the concentration ratios of the substances S1 to S4 will change, in accordance with these partition constants, in the region inside the biological material 7 and outside the biological material 7. According to the invention, this is utilized for separating the substances S1 to S4 from one another and from the other substances (not shown) and the biological material 7.

From FIG. 1 it can be gathered that in the case of the substances S1, S3 and S4, compared with substance S2, the mass exchange via the induced pores 6 in the membrane 8 is not limited by their size or shape. According to the invention, the diameter and the lifetime of the pore, which are defined by the experimental conditions which can be set individually, are utilized as a molecular sieve. Apart from their size and shape, substances also differ, however, in terms of other properties, which means that the procedure according to the invention utilizes not only the separation in terms of size and shape but also other material properties. For example, S1 is associated with the intracellular matrix 9, for example on the cell skeleton or an organelle etc. This substance therefore cannot pass into the region outside the biological material 7. It follows that $k_+1$, K1 and consequently the concentration outside the biological material 7 $[S1]_{[illegible]}$ must be set=0. S3 and S4 are not associated with intracellular matrix 9, i.e. are present in soluble form. However, they have different properties, for example in terms of their polarizability, hydrophobicity, aromaticity and electrostatics. Assuming the following relationships of the partition constants of the substances:

$$K_1=0<K_2<K_3<K_4,$$

with identical intracellular initial concentrations ($[S1]_{ia}=[S2]_{ia}=[S3]_{ia}=[S4]_{ia}$) and an extracellular initial concentration of zero in each case, this results in the following intracellular concentration distribution after the treatment:

$$[S1]_{ib}=[S1]_{ia}>[S2]_{ib}>[S3]_{ib}>[S4]_{ib}$$

and thus the following extracellular concentration distribution:

$$[S1]_{eb}=0<[S2]_{eb}<[S3]_{eb}<[S4]_{eb}$$

These changes in concentration are employed, according to the invention, to separate the substances S2 to S4 from S1, i.e. for selective separation. Via a suitable choice of the separation parameters it is also possible to separate S2 to S4 from one another, without a cell disruption and subsequent purification being required.

Of course it is equally possible according to the invention, by means of the above-described method, to separate substances from the liquid medium outside the biological material 7 from one another, via a selective enrichment in these substances inside the biological material 7 and a consequent depletion in this substance or these substances and an enrichment in another substance or other substances in the medium 5 present outside the biological material 7.

After the pulsed electric field E has been applied, the biological material 7, i.e. the stationary phase, together with the liquid medium present in the stationary phase, is separated from the liquid medium present outside the biological material 7, for example by means of centrifuging or filtration. This affords a mixture of S2, S3 and S4, which has been separated from S1, outside the biological material 7.

FIGS. 2 to 6 depict apparatuses for implementing the in situ separation method according to the invention, i.e. sample mount systems and in situ separation apparatuses 12. In each case, the figures show the arrangement of the two electrodes 11 with their terminals 17 and the electrode spacing 18. The voltage generators, frequency generators and pulse generators and sensors are not shown.

The electrode spacing 18 in the separation device 12 was 4 mm, the electrode material consisted of aluminum, the capacitance C was about 1.65 nF, the resistance of the treatment cell with an *E. coli* suspension and the HVA apparatus was about 2040 Ohms, the time constant was about 3.4 $\mu$s, and the pulse shape took the form of an exponential decrease.

The exponentially decreasing pulse shape used was generated by a capacitor discharge. In this arrangement, the capacitors were electrically charged using a lower current over a longer period and with the opposite, but constant current direction, in contrast to the electrical discharge of the capacitors. These electrical discharges generated DC voltage pulses which were crucial for the separation method. The pulse duration for exponentially decreasing pulse shapes is expressed by the time constant $(\tau)$:$\tau$=C R (C: capacitance; R: resistance).

Apart from the exponentially decreasing pulse shape, it is also possible, for example, to employ rectangular pulses, triangular pulses or sinusoidal pulses. It is also possible for the voltage of a pulse to fluctuate within the pulse, for example sinusoidally. Also conceivable is a continual polarity reversal of the successive pulses, so that DC voltage pulses are applied.

FIG. 2 shows an in situ separation apparatus 12 with a port 15 in the cover plate 13, which is used to introduce and to remove the sample. The separation apparatus 12 takes the shape of a cuboid, baseplate 14 and cover plate 13 of the cuboid being designed as nonconductive elements and two side walls being designed as electrodes 11. The two other side walls 28 and 29 (FIG. 6) are made of nonconductive material. Accordingly, the sample is transferred into the in situ separation apparatus 12 and is treated with pulsed electric fields E. In this procedure the sample, having been treated, is centrifuged to separate the medium present outside the biological material 7 from the medium within the biological material and the biological material itself. According to the invention, given suitable dimensions of the in situ separation apparatus 12, this can be effected directly by means of the in situ separation apparatus 12 itself. The supernatant with the desired substance(s) is then taken off. Alternatively, centrifuging of the sample can be carried out separately, after the treatment with pulsed electric fields E.

FIG. 3 essentially depicts the same separation apparatus 12 as shown in FIG. 2, except that two ports 20 and 21 are provided in the cover plate 13. One port 20 is used to introduce the sample, while the other port 21 is utilized to remove the sample. This enables a continuous separation process. In addition, either one of the ports 20 or 21 can serve for any pressure equalization required.

FIG. 4 depicts an in situ separation apparatus 12 with a port 15 in the cover plate 13 and a port 22 in the baseplate 14, a filter 23 being arranged in the port 22. The sample is introduced into the chamber 12 through the port 15 in the cover plate 13. After the pulsed electric field E has been employed, the liquid medium present outside the biological material 7 is removed via the filter 23 and the port 22 in the baseplate. The filter 23 allows the biological cells and thus the medium present in these cells to be retained, a continuous separation apparatus without centrifuging and consequently a particularly rapid and efficient separation method thus becoming possible.

FIG. 5 essentially depicts the in situ separation apparatus 12 already shown in FIG. 4, except that two ports 24, 25 are provided in the cover plate 13, the port 25 being fitted with a filter 26, and the port 24 being sealable by means of a cover 50. The separation apparatus 12 shown enables the continuous infeed of extracellular medium via the port 25 with the filter 26, no sample material being introduced into the chamber 12. Instead, the sample can be introduced separately via the sealable port 24. The liquid medium is removed via a filter 23 inserted into the port 22.

FIG. 6 depicts a cross section through the chambers of FIGS. 2 to. 5, illustrating the spacing 27 between the side walls 28 and 29.

FIG. 7 shows an in situ separation apparatus 12 which is designed as a sample mount system 31 and can, in particular, be utilized for disintegration. The sample mount system comprises at least two conductive elements, for example electrodes 11, which form faces arranged parallel to one another, which are designed as a bottom face, e.g. a baseplate 14, and a cover plate 13. Located on the baseplate 14 are at least four side walls 28 and 29 which are disposed vertically and together with the baseplate and cover plate 13, 14 form chambers within which the material to be treated can be stored. The electrode spacing 18 can be varied, so that the cover plate 13 seals the sample or at least comes into contact with the sample, thus making it possible to generate a voltage between the cover plate 13, which additionally may have a salient projecting into the sample medium, and the baseplate 14 across the sample present in liquid medium. The sample mount system 31 can be tailored to the conditions of the biological material to be studied and to its dimensions. This includes orders of magnitude of the field of microsystem technology and chip technology as well as the currently standard mount systems employed in laboratories. The sample mount system 31—like the in situ separation apparatus 12—is composed of conductive elements, the electrodes 11, and nonconductive elements such as, for example, the side walls 28 and 29. The geometry of the sample mount system can be chosen so as to enable the generation, as required, of both homogeneous and inhomogeneous electric fields. Application of the electric fields is effected via voltage generators, frequency generators and pulse generators which are suitably connected to the conductive elements, such as the electrodes 11, of the sample mount systems 31. By analogy to microplate systems which permit defined layer thicknesses to be generated it is advantageous for electronic disintegration arrays comprising defined electrode spacings 18 to be conceived so as to make it possible to prevent the formation of bubbles, which may affect the electric field. In this context it is particularly advantageous, for example, to integrate convex salients 33 into the conductive regions, such as the electrodes 11, of the cover 35. Bubble formation is thus very largely avoided, since the liquid medium 5 is displaced sideways as the cover 35 is lowered, and can flow down at the sides. This does assume, for example, that sample volumes are used which are larger than the volume of the sample mount well 37. Because of surface tension, a convex meniscus forms which can then be displaced without any bubbles being formed. To prevent cross-contamination during this operation it is advantageous, for example, to fit cross-contamination barriers 39 in such a way that the liquid medium 5 cannot, for example, as the cover 35 is lowered, contaminate the adjacent sample mount wells 37.

FIG. 8 shows a sample mount system 31 with which it is possible to obtain defined electrode spacings 18, even with sample volumes which are smaller than the volumes of the sample mount well 37. Formation of bubbles can be prevented by suitably shaped salients 33 being integrated into the conductive regions of the cover 35. For example, a convex-shaped tip of the salient 33 can be of advantage to reduce the formation of bubbles, but also, for example, to generate specifically shaped electric fields. Salients 41 with a concave-shaped tip are preferably provided with a channel 43 to allow any bubbles to escape. Lowering the cover 35 results in sideways displacement of the sample in the liquid medium 5 by the salients 33 in the sample mount well 37. In the event of any overflow, the cross-contamination barriers 39 offer protection against cross-contamination. Furthermore, it may be advantageous to integrate cavities 45 for the purpose of thermostating the sample mount systems 31. The cavities 45 can be formed by the side walls 28 and 29 and by the electrodes 11 and a sealing plate 47. Via suitable connections, thermostated liquids can ensure defined treatment temperatures. As another advantageous option, nonconductive or preferably conductive elements can be coupled directly to a thermostating arrangement.

FIG. 9 shows a sample mount system 31 with a hydraulic system 49. To allow a specific pressure to be built up which may have a beneficial effect on the electrical disintegration, or to build up a pressure in order, for example, to work in aqueous solutions above 100° C., it is advantageous, for example, to employ hydraulic systems 49 which press the cover 35 onto the sample mount wells 37. Alternatively, however, screw systems can be used to cover the sample mount system 31. Here it is advantageous for the salients 33 of the cover 35 to match the sample mount well 37 of the sample mount system 31 exactly or almost exactly, to establish a closed system. In such an arrangement, for example, guides 50 disposed, for example, at the upper rim of the sample well mount 37 are of advantage. Instead of an external hydraulic or screw-type system, such a system can also be combined directly with the sample mount system 31 or with the cover 35, as depicted in FIG. 9b.

FIG. 10 shows a chip 51 for the electrical disintegration or separation of e.g. cells. The design of the chip 51 can allow for a matrix of disruption units 55 to be integrated in its base 53, which can have a size of a few square millimeters or even square centimeters.

The disruption units 55 can be composed of conductive elements 57 and nonconductive elements 59 in whose center an inner chamber 61 for sample application is provided. As well as the actual electrical disintegration and/or separation of cells, other procedures, such as hybridization can be carried out on the chip 51. The conductive elements 57 and nonconductive elements 59 which form inner chambers 61 need not, however, be in the form of a matrix, they can also be conceived as individual sample mount systems 31. The disintegration benefits from the conductive elements 57 being separated from one another by nonconductive elements 59. Alternatively, the conductive elements 57 can, in positions where they come into contact with the liquid medium 5, be coated with a nonconductive layer. The dimensions in terms of height, and inside and outside dimensions, are variable. Likewise variable are the extent of the conductive elements 57 and of the nonconductive elements 59. As well as circular or square shapes of the horizontal cross section of the inner chamber 61 of the sample mount system 31, other geometric cross sections are of course conceivable, for example oval, rectangular, triangular. Since circular or oval or ellipsoidal shapes give rise to inhomogeneous electric fields in which the electric field line density is locally increased, these shapes can be used to advantage. If polyphase current is employed for disintegration, conductive elements 57 for three phases must be present. This can be achieved, for example, by a hexagonal horizontal cross section with conductive and nonconductive elements. In the above-mentioned embodiments it can be advantageous for sealing covers, e.g. snap-fit sealing covers to be integrated to achieve a further reduction in the risk of cross-contamination. Twist closures optionally fitted with O-rings can of course likewise be used to advantage.

FIG. 11 shows a longitudinal section through sample mount systems. 31. The sample mount systems are designed as container-like holding means 60. FIG. 11a shows a holding means 60 whose cross section is of rectangular shape. In this holding means 60, the side walls 28 and 29 are aligned virtually parallel to one another or as a truncated cone tapering toward the bottom. The side walls 28 and 29 are designed as conductive elements 57. The sealing plate 61 which seals the holding means 60 at the bottom is designed as a nonconductive element. FIG. 11b shows a holding means 60 which has a cover 35. The holding means 60 is of a frustoconical shape tapering toward the bottom. The side walls 28 and 29 are designed as conductive elements 57. The cross section of the sealing plate 61 has an almost half-round shape. The sealing plate 61 is designed as a nonconductive element 59. The cover 35 has a hinge 63 which links cover 35 and holding means 60. The cover 35 also includes a seal 65 which is fashioned as an inner circumferential dike on the side facing the holding means. The diameter of the circumferential dike of the seal 65 is chosen so as to ensure that the dike will seal the inner faces 67 of the holding means 60 in such a way that only very little or no material can escape. As the holding means 60 is of frustoconical shape tapering toward the bottom, the seal 65 must—as shown in FIG. 11b—be similarly angled to ensure optimal closure.

FIG. 12 shows a cross section through individual sample mount systems 31. In a sectional view, the sample mount systems 31 alternately comprise conductive elements 57 and nonconductive elements 59. FIG. 12a shows a holding means 60 of round cross section. The conductive elements 57 and the nonconductive elements 59 are arranged oppositely. FIG. 12b shows a sample mount system 31 of square cross section. The respective opposite sides respectively form the nonconductive elements 60 and the conductive elements 57. FIG. 12c shows a sample mount system 31 of hexagonal horizontal cross section. The sample mount system 31 shown is suitable for the use of polyphase current. Around the perimeter, the conductive elements 57 alternate with the nonconductive elements 60, the arrangement of the conductive elements 57 being such that phase 1 69 is located opposite itself. The phases 2 71 and the phases 3 73 are likewise arranged in such a way that they arise in opposite positions. According to possible designs of the conductive elements 57, these can be recessed into the wall 75 or form the wall 75, nonconductive elements 69 being disposed alternately in the wall 75.

FIG. 13 shows a longitudinal section through sample mount systems, in which holding means comprise conductive elements. The FIGS. 13a to 13d show cross sections of sample mount systems 31 in which, in each case, the entire holding means 60 is designed as a conductive element 57 or includes at least one conductive element 57 per holding means 60. The holding means 60 shown in longitudinal section can, for example, represent part of a modified microplate system. In the individual depressions of the microplate system, shown by way of example in FIG. 13 as holding means 60, the side walls 28 and 29, and the sealing plates 61, respectively, are designed as conductive elements 57 and nonconductive elements 59, respectively. FIG. 13a shows a sample mount system 31 comprising a plurality of holding means 60 arranged next to one another and a cover 35. The holding means 60 are designed throughout as a conductive element 57. Fitted into the cover. 35, which is designed as a nonconductive element 59, are conductive elements 57 in the form of rods 77 in such a way that the rods 77 run vertically through the cover 35 and project into the holding means 60. FIG. 13b shows a vertical cross section through a sample mount system 31 in which the holding means 60 is not designed throughout as a conductive element 57. The sample mount wells 37 are connected by nonconductive webs 79. FIG. 13b further shows that the sample mount wells 37 designed as conductive elements 57 can be insulated on the inside by means of a layer 81. This layer 81 can be applied to the inner walls of the side walls 28 or 29 and/or to the sealing plate 61 on that side which faces the sample mount well 37. The conductive element 57 can also take the form of a conductive membrane 83. The conductive membrane 83 forms the closure of the holding means 60, for example in the form of the sealing plate 61. FIG. 13c shows holding means 60 which, with the exception of the sealing plate 61, are designed as nonconductive elements 59; the sealing plate 61 is designed as a conductive element 57. The sealing plate 61 can be disposed in a planar, concave or convex manner. FIG. 13d shows a sample mount system 31 in which the side walls 28, 29 each form the conductive elements 57. The bottom of the respective sample wells 37 is designed as a nonconductive element 57, as are the webs 79; the sealing plate 61 can also be designed as a nonconductive membrane 85. The result of this type of arrangement is that conductive elements 57 and nonconductive elements 59 are positioned alternately in the sample mount system 31. A biological sample present in the sample mount well 37 could be disintegrated by the side walls 28, 29 designed as conductive elements 57. The vertical cross section shown can be part of a modified microplate system.

FIG. 14 shows a longitudinal section through covers 35 which comprise conductive elements 57. The conductive elements 57 are each inserted vertically into the cover 35. The conductive elements 57 in this arrangement are designed as rods 77. The rods 77 pass vertically through the cover 35. Provision can, for example, be made for the covers 35 to be used as lids for microplates or for modified microplates, as shown in a part view in FIG. 13. The rods 77, which are designed as conductive elements 57, are each disposed in the covers in such a way that their longer end points toward the possible holding means 60. That end of the rods 77 which projects into the solution can be of spherical shape or, for example, be T-shaped. T-shaped here means that that end of the rod 77 which projects into this sample is fitted with a crossbar, for example at an angle of 90°, whose length is less than that of the rod 77. FIG. 14a shows the detail from a cover 35 into which rods 77 are inserted. The rods 77 shaped as cylindrical metal rods are additionally fitted in the cover 35 with conductive plates 87. In the section pointing into the sample, the rods 77 can be enclosed by an insulation 89, said insulation 89 being applied in such a way that it the conductive plate 87 is likewise insulated on the side facing the holding means 60. FIG. 14b shows conductive elements 57 which are linked to one another via nonconductive elements 59 and which may form part of a cover 35, for example for holding means 60. The conductive elements 57 are designed as rods 77, for example in the form of metal rods having round cross sections. Alternately, however, the horizontal cross section of these metal rods can be rectangular or polygonal. At their bottom ends pointing toward the holding means 60, the rods 77 designed as metal rods have T-shaped terminations 91. FIG. 14c shows the assembly, depicted in FIG. 14b, of conductive elements 57 and nonconductive elements 59, some of the conductive elements 57 carrying an insulation 89. The insulation 89 encloses the rods 77 in such a way that the rods 77 on the side pointing upward project from the insulation 89 and in the side pointing downward the T-shaped termination 91 is exposed, i.e. not enclosed by an insulation 89. Furthermore, the assembly depicted in FIG. 14c, for example as part of a cover 35, does not include a conductive plate 57. FIG. 14c shows a cover 35 in which rods 77 and conductive plates 87 are embedded. The rods 77, for example designed as cylindrical metal rods, have spheres 93 at their bottom, longer end, i.e. that section of the rods 77 which projects into the holding means 60 terminates in a spherical shape. The spheres 93 can have the same diameter for all rods 77 or alternatively different diameters. The assemblies shown in FIG. 14, of conductive elements 57 and nonconductive elements 59, can form part of a cover 35. This cover 35 can cover, for example, prior art microplates, the disintegration requiring at least two conductive elements 57 for each well to be an effective connection. An alternative option, however, is to use the conductive elements 57 and nonconductive elements 59 shown in FIG. 14 and the conductive plate 87 to cover sample mount system 31, as depicted in FIG. 13b, 13c or 13d. In that case, placing the cover 35 onto a sample mount system 31 can be effected by each individual rod 77 formed in the cover 35 projecting into a single holding means 60, for example a sample mount well 37. Sample mount wells 37 and conductive elements 47 would an this case be arranged so as to be capable of being in effective connection. Alternately, however, provision can be made for the cover plate 35 with the rods 77 disposed therein to be inserted in such a way that a plurality of rods 77 are each disposed in one and the same sample mount well 37 so as to be capable of being in effective connection. The disintegration by means of voltage could in this arrangement take place between the individual rods 77.

Example: DNA and protein separation in *E. coli*

In a separation apparatus 12 according to FIG. 2, an *E. coli* cell suspension having a cell concentration of between one and ten times $10^9$ CFU/ml (colony-forming units) of *E. coli* strain DH5α (with the pET11b High Copy Plasmid and MIF insert, Macrophage Migration Inhibitory Factor) was treated with pulsed electric fields. The *E. coli* cells were suspended in PBS/EDTA solution with a pH of 7.4.

A 300 μl aliquot of the cell suspension was pipetted into the in situ separation apparatus 12. As a negative control, the same volume of the cell suspension was incubated in a reaction vessel under corresponding conditions. After the treatment with the pulsed electric fields (compare the parameter variations below), the temperature of the cell suspension was determined. Then the treated cell suspension was mixed and pipetted from the sample chamber. This was followed by one minute's centrifugation at 13000 rpm (16060 g) at 4° C., both the [lacuna] with pulsed electric fields and the negative control being centrifuged. Then the supernatant, i.e. the crude extract, was taken off and examined. This crude extract comprises the constituents released from the cells and thus reflects the extracellular concentration of these substances.

The DNA concentration of the crude extracts was determined in microtiter plates using the fluorescent dye SYBR-Green I (Molecular Probes) via a gel documentation system. This was done by mixing 50 µl of a DNA standard series (0.3 to 5 µg/ml) in aqueous solution or the respective crude extracts with 200 µl of SYBR-Green I diluted 5000-fold in 10 mM Tris/HCl; 1 mM EDTA solution, pH 7.5. After 5 minutes, the fluorescence of the samples upon excitation at 254 and 365 nm was determined via the pixel density, using the program Image Tool.

The protein concentration of the crude extracts was performed via the BioRad protein assay which is based on the protein detection according to Bradford. The reagent solution used was the BioRad protein reagent concentrate in 5-fold dilution with water. The protein solutions were admixed with the reagent solution in a ratio of 1:4. This corresponds to a microassay test solution. BSA was dissolved in water and suitably diluted for the sample solution. After incubation at room temperature for at least 10 minutes, the absorption of the samples at a wavelength of 590 nm was determined with a microtiter plate reader.

The separation efficiency of the method according to the invention was therefore determined via a determination of the protein concentration and DNA concentration of the crude extracts. The value of whichever variable parameter (protein concentration or DNA concentration) was the lowest was set to zero in each case, and the maximum values were used to calculate the ratio of the percentage values of extracellular proteins and extracellular DNA, the ratio of the zero values being set equal to one. This corresponds to the enrichment in proteins, compared with DNA, in the liquid medium outside the biological material. Since the passage of certain proteins through small pores from the intracellular into the extracellular medium proceeds mainly on the basis of their size, whereas DNA, especially genomic DNA, mainly passes into the extracellular medium only in the case of completely lysed cells, the enrichment also reflects the degree of cell disruption. In the case of the procedure according to the invention, cell disruption is of course undesirable, owing to its lack of selectivity.

According to the present example, therefore, the aim was to separate the protein from the DNA, i.e. an enrichment in protein in the liquid medium present outside the biological material, i.e. the cells, is desirable. The higher the degree of enrichment for extracellular protein, the more protein passed from the cell into the surrounding medium, and the more DNA remained in the cell, reflecting, as it were, a low degree of cell disruption.

In the following specific examples, the field strength, the pulse number (Pn) and thus both the treatment duration (Td) and the frequency (Fr) were varied (Pn=Td·Fr). The effect of the treatment temperature was also illustrated.

FIG. 15 shows how the extracellular protein enrichment depends on the field strength used. At a pulse number of 18000 with a treatment duration of 60 minutes, a frequency of 5 Hz and a temperature of 25° C., field strengths of 10; 30; 40; 60 V/cm were used. A field strength of about 7 kV/cm would have been required to reach the critical voltage $V_c$. The field strengths used were therefore far below the critical voltage $V_c$. At a field strength of from 30 to 50 V/cm, in particular, particularly good enrichment in protein was achieved in the medium present outside the biological material. This optimal field strength range does also depend, however, on the parameters, pulse number, treatment duration, frequency, temperature, solution and the biological material itself.

The FIGS. 16 and 17 illustrate how the extracellular protein enrichment depends on the pulse number. As the pulse number represents the product of treatment duration and frequency, two analyses were carried out, shown in FIGS. 16 and 17.

In a working example (FIG. 16) the frequency of the pulses was varied while the treatment duration was constant, pulse numbers of 900/9000/18000 and 90000; frequencies of 0.5/5/25 and 50 Hz; a treatment duration of 30 minutes; a field strength of 10 V/cm and a temperature of 25° C. being employed. As FIG. 16 shows, it was possible under these conditions, especially at a pulse number of 9000, to achieve particularly good enrichment in protein outside the biological material in the liquid medium.

In FIG. 17, the treatment duration was varied while the frequency was constant, pulse numbers of 15000/9000/18000; treatment durations of 5/30 and 60 minutes; a frequency of 5 Hz; a field strength of 40 V/cm and a temperature of 25° C. being used.

FIGS. 16 and 17 illustrate that the extracellular enrichment in protein compared with DNA and consequently the separation characteristics of the in situ separation method according to the invention has a range of optimal pulse numbers of from 5000 to 12000. This range does also depend on the parameters field strengths, treatment duration, frequency, temperature, solution and the biological material itself.

FIG. 18 shows how the extracellular enrichment in protein, compared with DNA, at constant pulse number depends on the treatment duration. Treatment durations of 0/3.3/6.7/33.3 and 66.7 minutes; frequencies of 0/2.5/5/25 and 50 Hz; a pulse number of 10,000; a field strength of 40 V/cm and a temperature of 25° C. were chosen. At the conditions chosen, treatment durations of up to 10 minutes were particularly beneficial in achieving enrichment in proteins compared with DNA. Direct effects of the frequency with respect to the induction of pores only become noticeable at frequency orders of magnitude which affect the pulse shape. The only effect which a higher frequency had in the present working examples, with the equipment used, was on the maximum achievable field strengths. Therefore, the dependence shown in FIG. 18 of the enrichment in proteins at constant pulse number and consequently variable frequency and treatment duration must be ascribed to the treatment duration. The data can therefore be correlated with the dependence of the enrichment on the pulse number at constant frequency (compare FIG. 17).

FIG. 19 illustrates the separation characteristics of the present method as a function of temperature. In this working example, the parameters were chosen as follows: temperature 10/30/45/55/50/65° C., field strength 24 V/cm; pulse number 18000, treatment duration 6 minutes and frequency 50 Hz.

The optimum of the temperature for the separation, studied by way of example, of proteins and DNA, being about 50° C., is significantly above the ambient temperatures which would be employed for an electroporation of E. coli. The disruption of the cells in this system would preferentially be carried out at temperatures above 70° C. The temperature optimum of the in situ separation methods according to the invention also depends on the parameters field strength, pulse number, frequency, treatment duration, solution and biological material itself.

The present data illustrate that substances are separated, in particular, according to the principle of a molecular sieve, i.e. in terms of their size. Substances whose size does not permit their passage through the pores induced according to the invention are retained. Smaller low molecular weight substances, on the other hand, pass through the pores into the medium present outside the biological material.

What is claimed is:

1. A method for the selective in situ enrichment in or separation of one or more substances from a substance mixture present in a liquid medium by means of a stationary and a mobile phase, wherein the stationary phase is a constituent of a biological material and the mobile phase is a liquid medium and wherein the biological material present in the liquid medium is subjected to pulsed electric fields having a field strength of up to 200 V/cm, and wherein the number of electric pulses is from greater than 10 to $7.2 \times 10^{14}$.

2. A method for the disintegration of biological material in a sample mount system, comprising at least one nonconductive element and two conductive elements, wherein a voltage is applied to the conductive elements and the biological material is subjected to a pulsed electric field having a field strength of up to 200 V/cm, and wherein the number of electric pulses is from greater than 10 to $7.2 \times 10^{14}$.

3. The method as claimed in claim 1, wherein an electric field line density is increased locally.

4. The method as claimed in claim 1, wherein the electric field has various pulse shapes.

5. The method as claimed in claim 1, wherein the electric voltage of the individual pulse fluctuates within itself.

6. The method as claimed in claim 1, wherein the electric field includes exponential, sinusoidal pulse shapes, rectangular pulses or triangular pulses or a combination thereof.

7. The method as claimed in claim 1, wherein a polyphase current is used.

8. The method as claimed in claim 7, wherein a three-phase current is used.

9. The method as claimed in claim 1, wherein the pulse number of the pulsed electric fields is at least 15.

10. The method as claimed in claim 1, wherein the field strength of the pulses is below the critical voltage $V_c$ across the membrane of the biological material.

11. The method as claimed in claim 1, wherein the field strength of the pulses is from 30 to 1 V/cm.

12. The method as claimed in claim 1, wherein the temperature at the biological disintegration is from 0 to 100° C.

13. The method as claimed in claim 1, wherein the temperature at the enrichment or separation is from −30° C. to +90° C.

14. The method as claimed in claim 1, wherein the treatment duration is from 2 seconds to 5 hours.

15. The method as claimed in claim 1, wherein the frequency of the pulses is from 0.01 Hz to 40 GHz.

16. The method as claimed in claim 1, wherein the pulse duration is from 25 ps to 1 min.

17. The method as claimed in claim 1, wherein the pulse duration is 15 ms and the pulse number is from 15 to 19,000, the temperature at the enrichment or separation is from 1° C. to 55° C., and the temperature at the biological disintegration is from 20 to 80° C.

18. The method as claimed in claim 1, wherein during or after the treatment with the electric field or both, one or more substances are released from the biological material.

19. The method as claimed in claim 1, wherein during or after the treatment with the pulsed electric fields or both, one or more substances are released from the biological material, are concentrated in the liquid medium outside the biological material and are then separated from the biological material.

20. The method as claimed in claim 1, wherein the substance(s) is (are) separated from the biological material by centrifuging the biological material and the liquid medium.

21. The method as claimed in claim 1, wherein the substance(s) is (are) separated from the biological material by filtration.

22. The method as claimed in claim 1, wherein during or after the treatment with the pulsed electric fields or both, one or more substances are concentrated in the biological material and in the process are abstracted from the liquid medium outside the biological material, and the liquid medium is then separated from the biological material.

23. The method as claimed in claim 1, wherein the substance is a nucleic acid or a derivative thereof.

24. The method as claimed in claim 1, wherein the substance is DNA or RNA.

25. The method as claimed in claim 1, wherein the substance is a protein, a peptide, a carbohydrate, a lipid, a pigment, a metabolite or a derivative thereof or a combination of these.

26. The method as claimed in claim 1, wherein the biological material is organisms, organs, tissues, organelles, membrane-enclosed compartments such as cells, particularly human cells, animal cells, vegetable cells, yeast cells or bacterial cells, viruses, cell nuclei, plastids, mitochondria, micelles or liposomes.

27. The method as claimed in claim 1, wherein the biological material is present in a solution or on a matrix or both.

28. The method as claimed in claim 1, wherein the solution has a high conductivity.

29. The method as claimed in claim 1, wherein the matrix is in direct contact with a conductive element (57) or is separated from the conductive element (57) via a liquid zone.

30. The method as claimed in claim 1, wherein the biological material is in contact with the conductive element (57).

31. The method as claimed in claim 1, wherein the electrical separation or disintegration or both is carried out in the presence of chemicals.

32. The method as claimed in claim 31, wherein the chemicals are added before or after the electrical separation or disintegration is carried out or both.

33. The method as claimed in claim 31, wherein the chemicals are chaotropic salts, detergents, enzymes, fluidity-modulating, lytic, protease-inhibiting nuclease-inhibiting chemicals or a combination thereof.

34. A sample mount system (31), comprising at least one nonconductive element (59) and at least two conductive elements (57), wherein at least one nonconductive element (59) is designed as a holding means and at least one conductive element (57) is designed as a cover (35), and wherein the cover (35) comprises at least one extension, salient or projection (77, 33, 41) which are suitable for preventing the formation of bubbles.

35. The apparatus as claimed in claim 34, wherein the extensions, salients or projections (77, 33, 41) are arranged so as to be capable of effective connection with the holding means (60).

36. A sample mount system (31) comprising at least one nonconductive element (59) and at least two conductive elements (57), wherein the sample mount system (31) includes at least one holding means (60), and wherein the entire holding means (60) is designed as a conductive element (57) or at least one conductive element (57) is present per holding means (60).

37. The apparatus as claimed in claim 36, wherein the holding means comprises at least one conductive element (57) designed as a cover (35).

38. The apparatus as claimed in claim 37, wherein the cover comprises at least one extension or projection (77).

39. The apparatus as claimed in claim 38, wherein the extensions or the projections (77) are arranged so as to be capable of effective connection with the holding means (60).

40. The apparatus as claimed in claim 34, wherein the conductive elements are electrodes (11) made of aluminum, gold, platinum, silver, gold or carbon or comprise these individually or in combination.

41. The apparatus as claimed in claim 34, wherein the nonconductive elements (59) are made of plastic, glass or silicon or comprise these individually or in combination.

42. An in situ separation apparatus (12), comprising a housing made of a baseplate (14), a cover plate (13), two side walls (28, 29) and two electrodes (11) designed as side walls, wherein at least one port (15) is present in the cover plate (13), and wherein filters (23, 26) are present in one or more of the ports (15, 20, 21; 22).

43. The apparatus as claimed in claim 42, wherein the electrodes (11) are made of aluminum, alloy steel, platinum, silver, gold or carbon or comprise these individually or in combination.

44. The apparatus as claimed in claim 42, wherein two ports (20, 21) are present in the cover plate (13).

45. The apparatus as claimed in claim 42, wherein a port (22) is present in the baseplate (14).

* * * * *